US009089407B2

(12) United States Patent
Schaer et al.

(10) Patent No.: US 9,089,407 B2
(45) Date of Patent: Jul. 28, 2015

(54) ANTIBACTERIAL COATINGS THAT INHIBIT BIOFILM FORMATION ON IMPLANTS

(71) Applicants: Massachusetts Institute of Technology, Cambridge, MA (US); University of Pennsylvania, Philadelphia, PA (US)

(72) Inventors: Thomas P. Schaer, Landenberg, PA (US); Suzanne Stewart, Kenneth Square, PA (US); Alexander M. Klibanov, Boston, MA (US)

(73) Assignees: Massachusetts Institute of Technology, Cambridge, MA (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/647,107

(22) Filed: Oct. 8, 2012

(65) Prior Publication Data

US 2013/0110237 A1 May 2, 2013

Related U.S. Application Data

(63) Continuation-in-part of application No. 11/107,412, filed on Apr. 14, 2005, which is a continuation of application No. 10/123,860, filed on Apr. 16, 2002, now Pat. No. 7,151,139.

(Continued)

(51) Int. Cl.
*A61F 2/02* (2006.01)
*A61L 27/34* (2006.01)
(Continued)

(52) U.S. Cl.
CPC . *A61F 2/02* (2013.01); *A01N 33/12* (2013.01); *A61L 27/34* (2013.01); *A61L 27/50* (2013.01)

(58) Field of Classification Search
CPC ........... A61F 2/02; A61L 27/34; A61L 27/50; A01N 33/12; A01N 25/10; A01N 25/34
See application file for complete search history.

(56) References Cited

U.S. PATENT DOCUMENTS

| 3,868,340 A | 2/1975 | Keegan |
| 4,327,073 A | 4/1982 | Huang |

(Continued)

FOREIGN PATENT DOCUMENTS

| EP | 0275015 | 7/1988 |
| WO | 9920105 | 4/1999 |

(Continued)

OTHER PUBLICATIONS

Nebojsa M. Milovic et al. "Immobilized N-Alkylated Polyethylenimine Avidly Kills Bacteria by Rupturing Cell Membranes With No Resistance Developed" Mar. 31, 2005, Wiley InterScience (www.interscience.wiley.com): Biotechnology and Bioengineering, vol. 90, No. 6, Jun. 20, 2005 p. 715-722.*

(Continued)

*Primary Examiner* — Peter D Mulcahy
(74) *Attorney, Agent, or Firm* — Pabst Patent Group LLP

(57) ABSTRACT

Orthopedic and dental implants coated with an antibacterial coating and methods of making and using, are described herein. The implant can be coated with a hydrophobic, polycationic antibacterial polymer. The polymer can be covalently or non-covalently associated with the surface; however, in particular embodiments, the polymer is non-covalently associated with the surface. As shown in the examples below, clinical observations, digital radiography, and a battery of well-accepted ex vivo analytical methods show that the presence of a hydrophobic polycationic polymer coating, such as N,N-dodecyl,methyl-PEI coating on the surface of a metal implant, was effective in eliminating the clinical signs of infection in vivo in a large animal infection model. Moreover, the coated plates supported bone healing, and in fact decreased healing times, even in the presence of significant bacterial contamination compared to a control.

22 Claims, 4 Drawing Sheets

Related U.S. Application Data

(60) Provisional application No. 60/285,883, filed on Apr. 23, 2001, provisional application No. 60/340,078, filed on Dec. 10, 2001, provisional application No. 60/368,495, filed on Mar. 29, 2002, provisional application No. 61/543,981, filed on Oct. 6, 2011.

(51) Int. Cl.
*A61L 27/50* (2006.01)
*A01N 33/12* (2006.01)

(56) References Cited

U.S. PATENT DOCUMENTS

| | | | |
|---|---|---|---|
| 4,404,196 A | 9/1983 | Daudt | |
| 4,460,747 A | 7/1984 | Horak | |
| 4,511,677 A | 4/1985 | Horton | |
| 4,542,125 A | 9/1985 | Gorman | |
| 4,847,088 A | 7/1989 | Blank | |
| 4,866,192 A | 9/1989 | Plueddemann | |
| 4,867,898 A | 9/1989 | Spaulding | |
| 4,888,434 A | 12/1989 | Sawaragi | |
| 4,898,957 A | 2/1990 | Plueddemann | |
| 4,921,701 A | 5/1990 | Blank | |
| 4,933,327 A | 6/1990 | Plueddemann | |
| 4,985,023 A | 1/1991 | Blank | |
| 4,990,338 A | 2/1991 | Blank | |
| 5,035,892 A | 7/1991 | Blank | |
| 5,045,322 A | 9/1991 | Blank | |
| 5,061,487 A | 10/1991 | Blank | |
| 5,064,613 A | 11/1991 | Higgs | |
| 5,073,298 A | 12/1991 | Gentle | |
| 5,079,004 A | 1/1992 | Blank | |
| 5,100,689 A | 3/1992 | Goldberg | |
| 5,112,903 A | 5/1992 | Sakakibara | |
| 5,126,138 A | 6/1992 | McGee | |
| 5,145,596 A | 9/1992 | Blank | |
| 5,169,561 A | 12/1992 | Gentle | |
| 5,169,625 A | 12/1992 | Blank | |
| 5,216,176 A | 6/1993 | Heindel | |
| 5,244,667 A | 9/1993 | Hagiwara | |
| 5,356,929 A | 10/1994 | Heindel | |
| 5,359,104 A | 10/1994 | Higgs | |
| 5,473,083 A | 12/1995 | Heindel | |
| 5,520,664 A | 5/1996 | Bricault | |
| 5,573,797 A | 11/1996 | Wilhoit | |
| 5,573,800 A | 11/1996 | Wilhoit | |
| 5,573,801 A | 11/1996 | Wilhoit | |
| 5,578,598 A | 11/1996 | Abe | |
| 5,656,611 A | 8/1997 | Kabanov | |
| 5,674,513 A | 10/1997 | Snyder, Jr. | |
| 5,716,709 A | 2/1998 | Ferguson | |
| 5,733,949 A | 3/1998 | Imazato | |
| 5,783,502 A | 7/1998 | Swanson | |
| 5,837,377 A | 11/1998 | Sheu | |
| 5,853,745 A * | 12/1998 | Darouiche | 424/423 |
| 5,861,149 A | 1/1999 | Ritter | |
| 6,013,615 A | 1/2000 | Zhou | |
| 6,022,553 A | 2/2000 | Anders | |
| 6,033,719 A | 3/2000 | Keogh | |
| 6,086,863 A | 7/2000 | Ritter | |
| 6,261,581 B1 | 7/2001 | Gebhardt | |
| 6,284,723 B1 | 9/2001 | Zhou | |
| 6,326,083 B1 | 12/2001 | Yang | |
| 2002/0051754 A1 | 5/2002 | Schroeder | |
| 2002/0068092 A1 | 6/2002 | Bosch | |
| 2003/0157193 A1 | 8/2003 | McDonald | |
| 2005/0003163 A1 * | 1/2005 | Krishnan | 428/190 |
| 2005/0154361 A1 | 7/2005 | Sabesan | |
| 2005/0220843 A1 | 10/2005 | DeWitt | |
| 2005/0271780 A1 * | 12/2005 | Schroeder et al. | 426/326 |

FOREIGN PATENT DOCUMENTS

| | | |
|---|---|---|
| WO | 0069264 | 11/2000 |
| WO | 0107090 | 2/2001 |

OTHER PUBLICATIONS

Hawley's Condensed Chemical Dictionary, 12th edition, Lewis, Sr. ed., Van Nostrand Reinhold Co., New York, pp. 21-22, 35 (1993).

Park, et al., 'Bacterial adhesion on PEG modified polyurethane surfaces' Biomaterials 19:851-859 (1998).

Tiller, et al., 'Designing surfaces that kill bacteria on contact' PNAS 98(11):5981-5985 (2001).

Behlau, et al., "Biocompatibility and biofilm inhibition of N,N-hexyl,methyl-polyethylenimine bonded to Boston keratoprosthesis materials", Biomaterials 32:8783-96 (2011).

* cited by examiner

ANTIBACTERIAL COATINGS THAT INHIBIT BIOFILM FORMATION ON IMPLANTS

CROSS-REFERENCE TO RELATED APPLICATIONS

This application is a continuation-in-part (CIP) of copending application Ser. No. 11/107,412, filed Apr. 14, 2005, which is a continuation of application Ser. No. 10/123,860, filed Apr. 15, 2002, which claims priority to U.S. Ser. No. 60/285,883, filed Apr. 23, 2001; U.S. Ser. No. 60/340,078, filed Dec. 10, 2001; and U.S. Ser. No. 60/368,495, filed Mar. 29, 2002, and also claims priority to Application Ser. No. 61/543,981, filed on Oct. 6, 2011, the entire contents of which are hereby incorporated by reference.

STATEMENT REGARDING FEDERALLY SPONSORED RESEARCH OR DEVELOPMENT

This invention was made with Government Support under Contact No. W911NF-07-D-0004, awarded to Massachusetts Institute of Technology by the Army Research Office. The Government has certain rights in the invention.

FIELD OF THE INVENTION

This invention is in the field of biomedical implant, such as orthopedic and dental implants, implants for ears, nose, and throat applications, and cardiovascular implants that exhibit antibacterial properties, prevent biofilm formation in vivo, and decrease healing times in mammals in the presence of infection.

BACKGROUND OF THE INVENTION

For many patients, surgical implantation of medical devices can be life-saving. However, implantation of these foreign bodies carries risk of infection. Although the risk of infection of these devices is in general only between 1 and 7%, the consequences of implant-associated infection are of great concern. Implant-associated infections are a major cause of fixation failure and result in increased morbidity, mortality, and treatment cost. The mortality of prosthetic valve endocarditis ranges up to 30%, and mortality rates associated with an infected aortic graft have approached 40%.

A critical step in the pathogenesis of device infections is bacterial adherence to the foreign body surface and the formation of a bacterial biofilm. A biofilm is defined as a structured community of bacterial cells enclosed in a self-produced polymeric matrix and adherent to an inert or living surface. Biofilms are characterized by high concentrations of organisms with little turnover and low metabolic activity. Bacteria within the biofilm communicate with each other through the elaboration and recognition of small molecules, a process called "quorum sensing". In orthopedic trauma for example, some 5-10% of orthopedic hardware facilitates host infection with increasing incidences for open fractures, combat related injuries, and revision joint replacements. As more soldiers from current armed conflicts around the globe survive serious blast trauma due to improved body armor, many sustain debilitating and life-threatening wound-related infections. Thus the need for improved implant surface protection in both civilian and military trauma patients has spurred recent research.

In the past, localized antimicrobial delivery systems have been developed for the treatment and prevention of implant-associated infections, including poly(methylmethacrylate) cements, biodegradable polymers, and regional limb perfusions. The elution kinetics of antimicrobials from these carrier systems typically exhibit an initial supra-therapeutic release that ultimately drops below the minimal inhibitory concentration (MIC). Such sub-MIC antimicrobial levels favor the emergence of drug-resistant bacterial strains. In addition, antimicrobials are typically ineffective in penetrating biofilms and may trigger quorum sensing and altered gene expression.

In the field of Ear Nose and Throat (ENT), for example, 8 out of 16 "failed" osteointegrating screws were found to have biofilm as determined by scanning electron microscopy (SEM). (Monksfiled P, Chapple I et al. J Laryngol Otol 125; 2011). Children undergoing treatment for otitis media, at an estimated cost of greater than $5 billion annually and a demographic distribution in the United States of 83% of children, will have at least one episode post-tympanostomy tube otorrhea, with 16% early postoperative, 26% late postoperative, 4% chronic and 7% recurrent. Fluorocarbon and silicone polymers constitute some of the substrates of tympanostomy tubes which are susceptible to bacterial adhesion.

The "Biofilm Hypothesis" states that persistent bacterial infection in the absence of positive culture and recalcitrance to antibiotic treatment is at the core of the failure of systemic therapies. In general the most common treatment for any implant infection today is re-operation, often requiring staged surgical interventions to clean or exchange the implant, debridement of infected tissues, followed by antimicrobial therapy, in some cases for several years.

In the United States alone, at least 100,000 out of over two million fixation device implants result in some form of post-operative infection. The cost of treating an implant-associated infection ranges from $30,000 to $300,000 and often involves repeated hospitalizations for treatment. Despite concerted efforts to resolve infections, there remains a very high rate of failure associated with initial infection treatment. Commonly, first course failure approaches 30% and results in a high rate of second and third course failure, multiplying costs and often leading to an ex-plant of the fixation device.

There exists a need for improved coatings that inhibit or prevent biofilm formation on implants, including orthopedic and dental implants, implants for ear, nose, and throat applications, and cardiovascular devices.

There also exists a need for improved coatings that inhibit or prevent biofilm formation on implants designed for long term implantation and/or decrease healing times in vivo in the presence of infection or other complications, e.g., open contaminated wounds and infections or closed wounds at risk for infection.

Therefore, it is an object of the invention to provide improved coatings for biomedical implants that inhibit or prevent biofilm formation.

It is also an object of the invention to provide improved coatings for implants that decrease healing times in vivo in the presence of infection or other complications, e.g., open contaminated wounds and infections or closed wounds at risk for infection.

SUMMARY OF THE INVENTION

Implants coated with an antimicrobial coating and methods of making and using, are described herein. The coating or the polymer in the coating is non-leaching, hemocompatible, and stable in vivo, e.g., non-degradable for a specified period of time. The material may be non-biodegradable or may degrade after a certain period of time. In one embodiment, the implant is an orthopedic or dental implant, such as implants that replace bone or provide fixation to bone, replace articulating surfaces of a joint, provide abutment for a prosthetic, or combinations thereof. In another embodiment, the implant is for ear, nose, and/or throat ("ENT") applications. In yet another embodiment, the implant is a cardiovascular device such as cardiac valves, alloplastic vessel wall supports, or total artificial heart implant.

The polymer can be covalently or non-covalently associated with the surface; however, in particular embodiments, the polymer is non-covalently associated with the surface. The polymer can be applied by a variety of techniques in the art including, but not limited to, spraying, wetting, immersing, dipping, such as dip coating (e.g., intraoperative dip coating), painting, or otherwise applying a hydrophobic, polycationic polymer to a surface of the implant.

The implant can be made from a variety of materials including, but not limited to, metallic materials (e.g., NiTi alloys, stainless steel, titanium or alloys thereof); metal oxides; non-degradable polymeric materials (e.g., polypropylene (PP), polyethylene (PE), polyacetylene, polystyrene, TEFLON®, poly(vinyl chloride) (PVC), polyolefin copolymers, poly(methyl methacrylate)); biodegradable/bioresorbable materials (e.g., collagen, cellulosic polymers, polysaccharides, poly(glycolic acid), poly(L-lactic acid) (PLLA), a polydioxanone (PDA), or racemic poly(lactic acid), polyurethane (PU), polycarbonates, polyetherketone (PEEK), polyesters (e.g., poly(ethylene terephthalate), polyamides (nylon); fluoroplastics, and other materials, such as porcelain; ceramic; allogenic or xenogenic bone or bone matrix; genetically engineered bone; and combinations thereof.

In some embodiments, the implants is a prostheses, implant as artificial substitutes for body parts, and materials inserted into tissue for functional, cosmetic, or therapeutic purposes. Prostheses can be functional, as in the case of artificial arms and legs; cosmetic, as in the case dermal filler; and therapeutic as in the case of implants surgically inserted or grafted into the body and intended to replace non-functioning organs. Exemplary orthopedic and dental implants include, but are not limited to, wires, Kirschner wires, bone plates, screws, pins, tacks, rods, nails, nuts, bolts, washers, spikes, buttons, wires, fracture plates, reconstruction and stabilizer devices, endo- and exoprostheses (articulating and non-articulating), intraosseous transcutaneous prostheses, spacers, mesh, implant abutments, anchors, barbs, clamps, suture, interbody fusion devices, tubes of any geometry, scaffolds, and combinations thereof. Exemplary dental implants include root devices, such as those made from titanium, used to support restorations that resemble a tooth or group of teeth to replace missing teeth.

Exemplary cardiovascular implants are cardiac valves or alloplastic vessel wall supports, total artificial heart implants, ventricular assist devices, vascular grafts, stents, electrical signal carrying devices such as pacemaker and neurological leads, defibrillator leads, and the like.

Exemplary ENT implants include, but are not limited to, ear tubes, ventilation tubes, endotracheal tubes, cochlear implants and bone anchored hearing devices.

In some embodiments, the antimicrobial coating is a hydrophobic, polycationic polymer. In some embodiments, the hydrophobic polycationic polymer is an N-alkylated polyethylenimine with various alkyl chain lengths such as N,N-dodecyl,methyl-polyethylenimine or N,N-hexyl,methyl-polyethylenimine. In other embodiments, the polymer is an poly(4-vinyl-N-alkylpyridine).

As shown in the examples below demonstrating in vivo efficacy, clinical observations, digital radiography, and a battery of well-accepted ex vivo analytical methods show that the presence of a hydrophobic polycationic polymer coating, such as N,N-dodecyl,methyl-PEI coating on the surface of a metal implant, was effective in eliminating the clinical signs of infection in vivo in a large animal infection model. Moreover, the coated plates supported bone healing, and in fact decreased healing times, even in the presence of significant bacterial contamination compared to a control. Animals treated with coated implants also exhibited overall less inflammation of the soft tissue envelope, more bridging callus formation, no macroscopic evidence of purulent debris, and a macroscopically more stable osteotomy at one month.

The implants described herein can be used to treat open fractures or wounds where infection is present or which are prone to infection, particular traumatic injuries, such as battlefield injuries or injuries that occur at a location which is removed from medical facilities. In such situations, treatment must be rendered immediately in order to stabilize the fracture. The conditions under which treatment is rendered are typically not sterile and so the potential for infection is high. Further, it may be some time before the patient reaches a medical facility where the wound can be closed. Therefore, the use of the implants descried herein can be used to effectively treat such injuries in the presence of infection.

DETAILED DESCRIPTION OF THE INVENTION

I. Definitions

Figure 1:
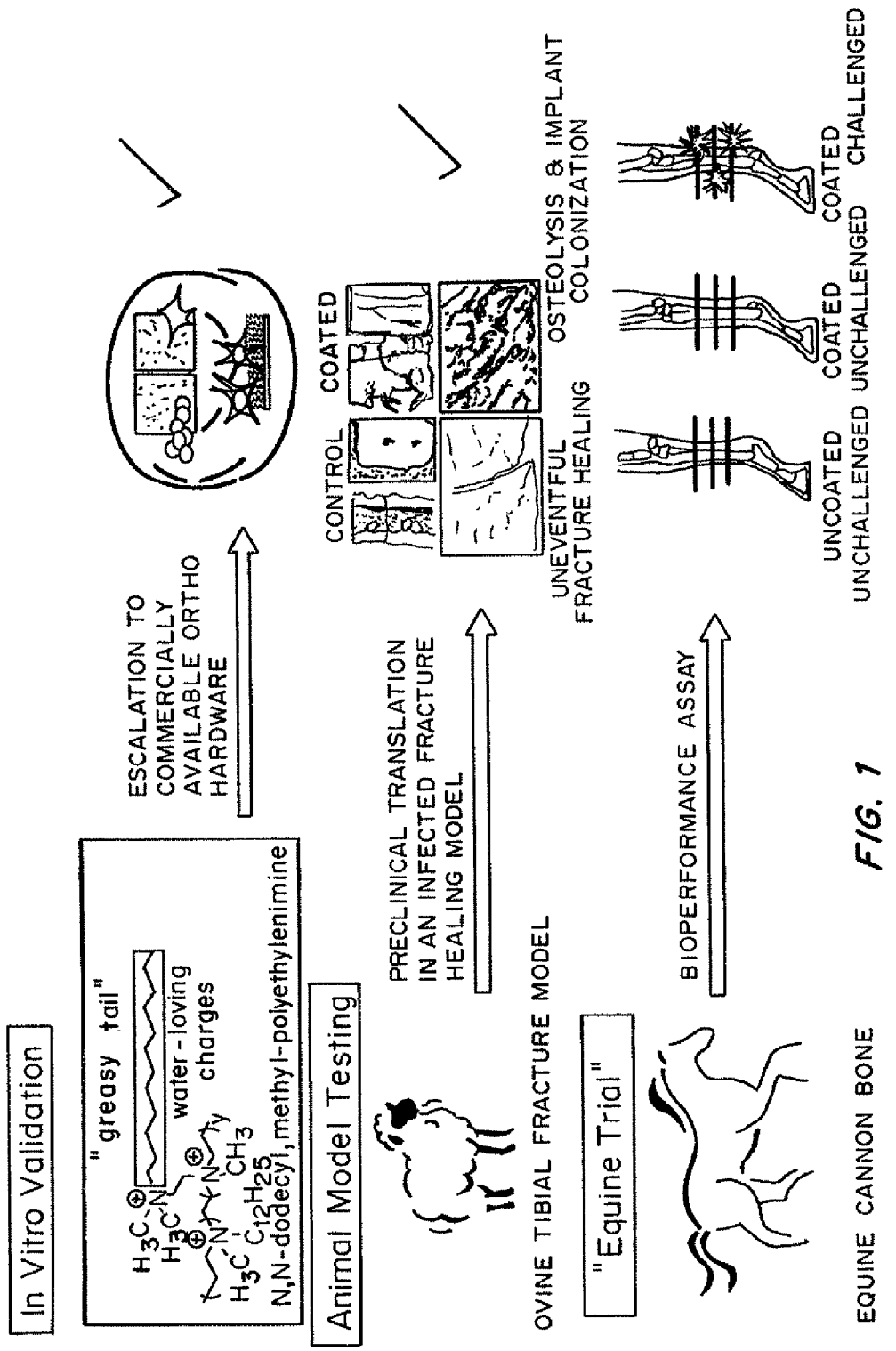
FIG. 1 a schematic showing the protocols for in vitro validation, animal model testing, and equine trial of coated implants.

"Biocompatible", as used herein, means the ability of an implant to perform its desired function with respect to a medical therapy, without eliciting any undesirable local or systemic effects in the recipient or beneficiary of that therapy.

"Contacting" as used herein refers to any means for coating a hydrophobic polymer, such as a hydrophobic polycationic polymer, on a surface. Contacting can include, but is not limited to, intraoperative dip-coating, spraying, wetting, immersing, dipping, painting, bonding or adhering, stepwise surface derivatization, or otherwise providing a surface with a compound with the hydrophobic, polycationic polymer. The polymer can be covalently or non-covalently attached to the surface. In some embodiments, the polymer is non-covalently associated with the surface.

"Coating", as used herein, refers to any temporary, semi-permanent or permanent layer, covering or surface. A coating can be applied as a gas, vapor, liquid, paste, semi-solid or solid. In addition a coating can be applied as a liquid and solidified into a hard coating. Elasticity can be engineered into coatings to accommodate pliability, e.g. swelling or shrinkage, of the surface to be coated.

A "component" is a part of an apparatus that is structurally integrated with that apparatus. A component may be applied to a surface of an apparatus, contained within the substance of the apparatus, retained in the interior of the apparatus, or any other arrangement whereby that part is an integral element of the structure of the apparatus. As an example, the silicone covering surrounding the mechanical part of a pacemaker is a component of the pacemaker. A component may be the lumen of an apparatus where the lumen performs some function essential to the overall function of the apparatus. The lumen of a tissue expander port is a component of the tissue expander. A component can refer to a reservoir or a discrete area within the apparatus specifically adapted for the delivery of a fluid to a surface of the apparatus. A reservoir within an implantable drug delivery device is a component of that device.

The phrase "effective amount", as used herein, generally refers to the amount of the antimicrobial coating applied to the implant in order to provide one or more clinically measurable endpoints, such as uncomplicated fracture healing or tissue remodeling in the presence of bacterial contamination or infection.

An "implant" is any object intended for placement in the body of a mammal, such as a human, that is not a living tissue. Implants include naturally derived objects that have been processed so that their living tissues have been devitalized. As an example, bone grafts can be processed so that their living cells are removed, but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components. The term "implant" can be applied to the entire spectrum of medical devices intended for placement in a human body or that of a mammal, including orthopedic applications, dental applications, ear, nose, and throat ("ENT") applications, and cardiovascular applications.

In some embodiments, the implant is an orthopedic implant. An "orthopedic implant" is defined as an implant which replaces bone or provides fixation to bone, replaces articulating surfaces of a joint, provides abutment for a prosthetic, or combinations thereof. In another embodiment, the implant is a dental implant. In other embodiments, the implant is an ENT implant. An ENT implant is defined as an implant which restores structure and/or function to ears, nose, and/or throat. In other embodiments the implant is a cosmetic implant. A cosmetic implant is defined as an implant that provides tissue support for example dermal fillers or structural support such as chins for reconstructive craniomaxillofacial surgery.

The implants can be made of a variety of biocompatible materials, including: metals, ceramics, polymers, gels and fluids not normally found within the human body. Examples of polymers useful in fabricating medical devices/implants include such polymers as silicones, rubbers, latex, plastics, thermoplastics, polyanhydrides, polyesters, polyorthoesters, polyamides, polyacrylonitrile, polyurethanes, polyethylene, polytetrafluoroethylene, polyethylenetetraphthalate, polyphazenes, and fluoroplastics. Medical devices can also be fabricated using certain naturally-occurring materials or treated naturally-occurring materials. Implants can include any combination of artificial materials, combinations selected because of the particular characteristics of the components. For example, a hip implant can include a combination of a metallic shaft to bear the weight, a ceramic artificial joint and a polymeric glue to affix the structure to the surrounding bone. Implants can reside wholly in the body or partly in the body and partly outside the body. Implants can be intended for short-term or long-term residence where they are positioned.

The terms "infectious microorganisms" or "infectious agents" as used herein refers to disease causing or contributing bacteria (including Gram-negative and Gram-positive organisms, such as Staphylococci (e.g. *Staphylococcus aureus, Staphylococcus epidermis*), *Enterococcus* sp. (e.g., *E. faecalis*), *Pseudomonas* sp. (e.g., *P. aeruginosa*), *Escherichia* sp. (e.g., *E. coli*), *Proteus* sp. (e.g., *P. mirabilis*)), fungi (including *Candida albicans*), viruses, and protists.

The term "soluble" refers to the ability to be loosened or dissolved.

The term "surface" or "surfaces" can mean any surface of any solid or semi-solid material, including glass, plastics, metals, polymers, and like. It can include surfaces constructed out of more than one material, including coated surfaces.

Biofilm formation with health implications can involve those surfaces in all health-related environments, including surfaces found in medical environments and those surfaces in industrial or residential environments that are involved in those functions essential to well-being like nutrition, sanitation and the prevention of disease.

A surface of an article adapted for use in a medical environment can be capable of sterilization using autoclaving, biocide exposure, irradiation or gassing techniques like ethylene oxide exposure. Surfaces found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, ear tubes, peripherably insertable central venous catheters, dialysis catheters, long term tunneled central venous catheters peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts.

The term 'Gram-positive bacteria' is an art recognized term for bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcessus, Mycobacterium avium complex, Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B *streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius*, and *Streptococcus sanguis*.

The term "Gram-negative bacteria" is an art recognized term for bacteria characterized by the presence of a double membrane surrounding each bacterial cell. Representative Gram-negative bacteria include *Acinetobacter calcoaceticus, Actinobacillus actinomycetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chlamydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pallidum endemicum, Treponema pertenue, Veillonella* spp., *Vibrio cholerae, Vibrio vulnificus, Yersinia enterocolitica, Yersinia pestis*.

"Non-leaching", as used herein, generally means that no appreciable amount of the bactericidal polymer is released from the coating on the implant over a particular time period. One way to ascertain that a coated material is non-leaching is to shake it in an aqueous solution over a certain period of time, e.g., 24 hours, or a week, or a month, then remove it, and inoculate the remaining solution with representative bacteria. If the bacteria thus introduced grow and multiply similarly to (e.g., statistically indistinguishably from) those in controls (i.e., the fresh aqueous solution and/or that fresh solution incubated with the uncoated material for the same time period and under the same conditions as the coated material), then the coating is considered non-leaching. In one embodiment, "non-leaching" means that the implant retains greater than 50%, 55%, 60%, 65%, 70%, 75%, 80%, 85%, 90%, 95%, 99% by weight of the coating over the course of 7, 14, 30, 60, 90, 100, or greater in phosphate buffered saline (PBS), media, serum, or in vivo.

"Substantially non-toxic", as used herein, means a surface that is substantially non-hemolytic and substantially non-cytotoxic.

"Antimicrobial" refers to the ability of a material to inhibit the growth of (i.e., bacteriostatic) or kill (i.e., bacteriocidal) microorganisms, such as bacteria, yeast, fungi, mycoplasma, viruses or virus infected cells, and/or protozoa.

"In vivo stability" refers to materials which are not degraded in an organism over a defined period of time.

"Non-degradable" or "stable", as used herein synonymously, refers to material compositions that do not react within a biological environment either hydrolytically, reductively, enzymatically or oxidatively to cleave into smaller pieces. Preferably non-degradable materials retain >25%, >50%, >75%, >90%, >95%, or >99% of their original material properties such as surface contact angle, non-fouling, and/or antimicrobial activity for a time of 7, 14, 30, 120, 365, or 1000 days in media, serum, or in vivo.

"Coating", as used herein, refers to any temporary, semi-permanent or permanent layer, or layers, treating or covering a surface. A coating can be a gas, vapor, liquid, paste, semi-solid or solid. In addition, a coating can be applied as a liquid and solidified into a solid coating.

"Substantially hemocompatible", as used herein, means that the composition is substantially non-hemolytic, in addition to being non-thrombogenic and non-immunogenic, as tested by appropriately selected assays for thrombosis, coagulation, and complement activation as described in ISO 10993-4.

"Hydrophobic", as used herein, generally means that the material has a greater affinity for, and thus solubility in, organic solvents compared to water. Hydrophobicity can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is attained in the organic solvent than in water, then the compound is considered hydrophobic. Hydrophobicity can also be evaluated by measuring the surface contact angle. In some embodiments, the surface angle is greater than about 70, 75, 80, 85, 90, 95, 100, 105, 110, or 115 degrees when measured using a goniometer.

An amphipathic molecule or compound is an art recognized term where one end of the molecule or compound is polar and another end is non-polar.

The term "polar" is art-recognized and generally means that the compound has a dipole moment greater than zero. A polar compound contains substances with asymmetric charge distribution (i.e., electron density). In general, a non-polar solvent will dissolve non-polar compounds, and a polar solvent will dissolve polar compounds, e.g. water, a polar substance, dissolves other polar substances, for example, sugars, amino acids, most salts, and proteins. An amphipathic (Amphiphilic) compound has a portion which is soluble in aqueous solvents, and a portion which is insoluble aqueous solvents. For example, sodium dodecyl sulfate, $CH_3(CH_2)_{11}$ OSO₃Na is amphipathic (or amphiphilic) because its polar sodium sulfate moiety is highly soluble in water and its nonpolar dodecyl moiety is highly insoluble in water.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (.sigma.) constant. This well known constant is described in many references, for instance, J. March, Advanced Organic Chemistry, McGraw Hill Book Company, New York, (1977 edition) pp. 251-259. The Hammett constant values are generally negative for electron donating groups ($\sigma[P]=-0.66$ for $NH_2$) and positive for electron withdrawing groups ($\sigma[P]=0.78$ for a nitro group), $\sigma[1]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl(alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and preferably 20 or fewer, more preferably 10 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulihydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or nonaromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

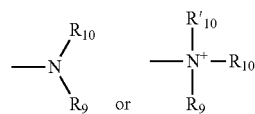

wherein $R_9$, $R_{10}$, and $R'_{10}$ each independently represent a group permitted by the rules of valence.

The term "acylamino" is art-recognized and refers to a moiety that can be represented by the general formula:

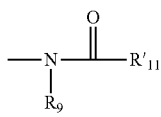

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

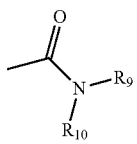

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_8$—$R_8$, wherein m and $R_8$ are defined above. Representative alkylthio groups include methylthio, ethyl thio, and the like.

The term "carbonyl" is art recognized and includes such moieties as can be represented by the general formula:

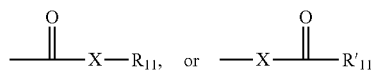

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R'_{11}$ is hydrogen, the formula represents a "thiolformate." On the other hand, where X is a bond, and $R_{11}$ is not hydrogen, the above formula represents a "ketone" group. Where X is a bond, and $R._{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, $(CH_2)_m$—$R_8$, where m and $R_8$ are described above.

The term "sulfonate" is art recognized and includes a moiety that can be represented by the general formula:

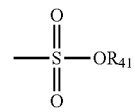

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

The term "sulfate" is art recognized and includes a moiety that can be represented by the general formula:

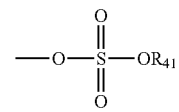

in which $R_{41}$ is as defined above.

The term "sulfonylamino" is art recognized and includes a moiety that can be represented by the formula

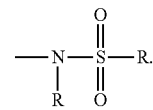

The term "sulfamoyl" is art-recognized and includes a moiety that can be represented by

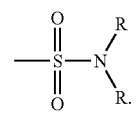

The term "sulfonyl", as used herein, refers to a moiety that can be represented by the general formula:

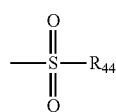

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

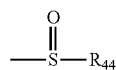

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2.sup.nd ed.; Wiley: New York, 1991).

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

II. Compositions

Orthopedic implants coated with one or more non-leaching, antimicrobial, hydrophobic polymers particularly one or more polycationic polymers, are described herein. "Polycationic polymer", as used herein, refers to polymers whose net charge is electropositive.

The coated implants described herein show no evidence of leaching of the antimicrobial coating at 90 days post-op as plates coated with the antimicrobial polymer(s) exhibit the same or a similar level of antimicrobial activity compared to freshly prepared plates. In one embodiment, the coated implants described herein, when implanted in vivo, result in decreased healing times or tissue remodeling in the presence of bacterial contamination or infection compared to a control.

A. Implants

Implants coated with one or more hydrophobic, polycationic polymer coatings are described herein. In one embodiment, "implant" as used herein refers to a macroscopic composition including an device for implantation or a surface of a device for implantation and one or more hydrophobic, polycationic polymer coatings. In this embodiment, the term "implant" does not encompass nanoparticles and/or microparticles. "Macroscopic" as used herein generally refers to devices, implants, or compositions that can be viewed by the unaided eye.

The implants can be formed from a variety of materials include polymers, metals, glass, ceramics, and combinations thereof.

In one embodiment, the implant is an orthopedic implant. An "orthopedic implant" is defined as an implant which replaces bone or provides fixation to bone, replaces articulating surfaces of a joint, provides abutment for a prosthetic, or combinations thereof or assists in replacing bone or providing fixation to bone, replacing articulating surfaces of a joint, providing abutment for a prosthetic, and combinations thereof.

Suitable orthopedic implants include, but are not limited to, wire, Kirschner wire, bone plates, screws, pins, tacs, rods, nails, nuts, bolts, washers, spikes, buttons, wires, fracture plates, reconstruction and stabilizer devices, endo- and exo-prostheses (articulating and non-articulating), intraosseous transcutaneous prostheses, spacers, mesh, implant abutments, anchors, barbs, clamps, suture, interbody fusion devices, tubes of any geometry, scaffolds, and combinations thereof.

In other embodiments, the implant is an ear, nose, and/or throat ("ENT") implant. Exemplary ENT implants include, but are not limited to, ear tubes, endotracheal tubes, ventilation tubes, cochlear implants and bone anchored hearing devices.

In other embodiments, the implant is a cardiovascular implant. Exemplary cardiovascular implants are cardiac valves or alloplastic vessel wall supports, total artificial heart implants, ventricular assist devices, vascular grafts, stents, electrical signal carrying devices such as pacemaker and neurological leads, defibrillator leads, and the like.

The implant(s) can be prepared from a variety of materials. In some embodiments, the material is biocompatible. In some embodiments, the material is biocompatible and non-biodegradable. Exemplary materials include metallic materials, metal oxides, polymeric materials, including degradable and non-degradable polymeric materials, ceramics, porcelains, allogeneic, xenogenic bone or bone matrix; genetically engineered bone; and combinations thereof.

Suitable metallic materials include, but are not limited to, metals and alloys based on titanium (such as nitinol, nickel titanium alloys, thermo-memory alloy materials), stainless steel, tantalum, pal ladium, zirconium, niobium, molybdenum, nickel-chrome, or certain cobalt alloys including cobalt-chromium and cobalt-chromium-nickel alloys such as ELGILOY® and PHYNOX®.

Suitable ceramic materials include, but are not limited to, oxides, carbides, or nitrides of the transition elements such as titanium oxides, hafnium oxides, iridium oxides, chromium oxides, aluminum oxides, and zirconium oxides. Silicon based materials, such as silica, may also be used.

Suitable polymeric materials include, but are not limited to, polystyrene and substituted polystyrenes, polyethylene, polypropylene, polyacetylene, polystyrene, TEFLON®, poly (vinyl chloride) (PVC), polyolefin copolymers, poly(urethane)s, polyacrylates and polymethacrylates, polyacrylamides and polymethacrylamides, polyesters, polysiloxanes, polyethers, poly(orthoester), poly(carbonates), poly(hydroxyalkanoate)s, polyfluorocarbons, PEEK®, Teflon® (polytetrafluoroethylene, PTFE), silicones, epoxy resins, Kevlar®, Dacron® (a condensation polymer obtained from ethylene glycol and terephthalic acid), nylon, polyalkenes, phenolic resins, natural and synthetic elastomers, adhesives and sealants, polyolefins, polysulfones, polyacrylonitrile, biopolymers such as polysaccharides and natural latex, collagen, cellulosic polymers (e.g., alkyl celluloses, etc.), polysaccharides, poly(glycolic acid), poly(L-lactic acid) (PLLA), a polydioxanone (PDA), or racemic poly(lactic acid), polycarbonates, (e.g., polyamides (nylon); fluoroplastics, carbon fiber, and blends or copolymers thereof.

In one embodiment, the orthopedic implant is one designed to promote healing of any bone or bones in the mammalian skeleton in the presence of infection. The implants can be used to promote healing of large bones, such as the femur. In other embodiments, the implant is designed to restore structure, and/or function and/or to promote healing of the cardiovascular system (e.g., heart), ears, nose, and/or throat, particularly in the presence of bacterial contamination or infection.

B. Hydrophobic Polymers

The implants described herein are coated with an antimicrobial hydrophobic polymer. In particular embodiments, the hydrophobic polymer is a hydrophobic, polycationic polymer. The coating or the polymer in the coating is preferably non-leaching, hemocompatible, and stable in vivo, e.g., non-biodegradable for a specified period of time. The material may be non-biodegradable or may biodegrade after a certain period of time.

In some embodiments, the hydrophobic polymer is a polycationic polymer. Suitable cationic polymers include, but are not limited to, poly(4-vinyl-N-alkylpyridinium halides), poly (methacryloyloxydidecylpyridinium halides), N-alkyl branched or linear polyethylene imine (PEI), and combinations thereof.

Suitable poly(4-vinyl-N-alkylpyridinium halides) include polymers having the formula:

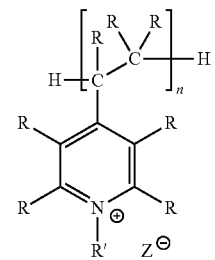

Wherein, R represents individually for each occurrence hydrogen, alkyl, alkenyl, alkynyl, acyl, aryl, carboxylate, alkoxycarbonyl, aryloxycarbonyl, carboxamido, alkylamino, acylamino, alkoxyl, acyloxy, hydroxyalkyl, alkoxyalkyl, aminoalkyl, (alkylamino)alkyl, thio, alkylthio, thioalkyl, (alkylthio)alkyl, carbamoyl, urea, thiourea, sulfonyl, sulfonate, sulfonamido, sulfonylamino, or sulfonyloxy;

R' represents independently for each occurrence is substituted or unsubstituted alkyl, heteroalkyl, cycloalkyl, heterocycloalkyl, aryl, or heteroaryl; an alkylidene tether to a surface; or an acyl tether to a surface;

Z represents independently for each occurrence Cl, Br, or I; and n is an integer less than or equal to about 5000, 4500, 4000, 3500, 3000, 2500, 2000, or 1500.

In some embodiments, R' is $C_4$-$C_{12}$, preferably $C_6$-$C_{12}$, more preferably $C_6$-$C_{10}$.

In other embodiments, the polymer is a N,N-dialkyl branched or linear polyethylene imine (PEI) having the chemical structure shown below:

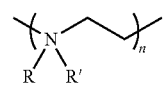

wherein R and R' are independently substituted or unsubstituted alkyl, heteroalkyl, cycloalkyl, heterocycloalkyl, aryl, or heteroaryl and n is an integer less than or equal to about 5000, 4500, 4000, 3500, 3000, 2500, 2000, or 1500.

In some embodiments, R and R' are the same. In other embodiments, R and are different. In particular embodiments, R and R' are different where R is a methyl group and R' is a $C_6$-$C_{25}$, alkyl group, preferably $C_6$-$C_{20}$, more preferably $C_6$-$C_{18}$, most preferably $C_8$-$C_{18}$. In particular embodiments, R' is hexyl, octyl, decyl, or dodecyl. Exemplary polymers include, but are not limited to, N,N-hexyl,methyl-PEI and N,N-dodecyl,methyl-PEI. In contrast, unmodified polyethylene imine (PEI) is generally characterized as a hydrophilic polymer.

In still other embodiments, the polymer has the structural formula:

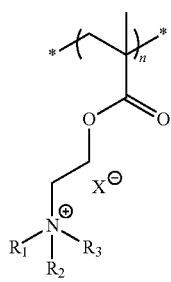

wherein each of $R_1$-$R_3$ are independently hydrogen or substituted or unsubstituted alkyl, heteroalkyl, cycloalkyl, heterocycloalkyl, aryl, or heteroaryl, and n is an integer less than or equal to about 5000, 4500, 4000, 3500, 3000, 2500, 2000, or 1500.

In some embodiments, at least one of $R_1$-$R_3$ is an alkyl group. In one embodiment, $R_1$ and $R_3$ are lower alkyl, such as methyl, and $R_2$ is at least $C_{10}$-$C_{25}$, preferably $C_{15}$-$C_{25}$, more preferably $C_{20}$-$C_{25}$, most preferably $C_{22}$.

In still other embodiments, the polymer has the structural formula:

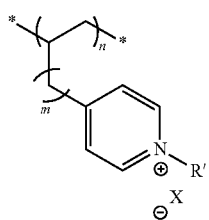

wherein R is as defined above and is preferably $C_{10}$-$C_{25}$, preferably $C_{15}$-$C_{25}$, more preferably $C_{20}$-$C_{25}$, most preferably $C_{18}$, n is an integer less than or equal to about 5000, 4500, 4000, 3500, 3000, 2500, 2000, or 1500, and m is an integer from 1-10, preferably 3-10, more preferably 3-6. In some embodiments, m is 3.

In still other embodiments, the polymer has the structural formula:

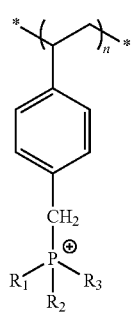

wherein each of $R_1$-$R_3$ are independently as defined above for R and n is an integer less than or equal to about 5000, 4500, 4000, 3500, 3000, 2500, 2000, or 1500. In one embodiment, $R_1$-$R_3$ are $C_6$-$C_{10}$, preferably $C_8$-$C_{10}$, more preferably about $C_8$.

The polymer can be any molecular weight provided the polymer is antimicrobial, i.e., bacteriostatic and/or bactericidal. The polymers above generally have a weight average molecular weight of at least 10,000 g/mol, at least 20,000 g/mol, at least 25,000 g/mol, at least 40,000 g/mol, at least 50,000 g/mol, at least 60,000 g/mol, at least 75,000 g/mol, at least 90,000 g/mol, at least 100,000 g/mol, at least 120,000 g/mol, at least 150,000 g/mol, at least 200,000 g/mol, at least 250,000 g/mol, at least 400,000 g/mol, at least 500,000 g/mol, or at least 750,000 g/mol.

The polymer can be covalently and/or non-covalently associated with the surface. In one embodiment, the polymer is non-covalently associated with the surface. Non-covalent interactions include, but are not limited to, hydrophobic interactions, hydrophilic interactions, ionic interactions, hydrogen bonding, and binding partners which interact non-covalently. The hydrophobic nature of the polymer repels water and other aqueous solvent thus preventing dissolution of the polymer from the surface of the implant.

In some embodiments, the polymer, such as a polycationic polymer, is non-covalently associated with the surface. In other embodiments, the polymer is non-covalently adhered or attached to the surface and is applied to the surface in the absence of a polyanionic polymer (e.g., polyelectrolyte complex). The polymer composition may contain one or more additives which modify the mechanical or physical properties of the polymer, such as plasticizers.

The coated implants exhibit antimicrobial properties and prevent biofilm formation in vivo. For example, in one embodiment, bacterial cells are sprayed onto a substrate coated with a polymer. The percentage of bacteria killed is at least 90%, 91%, 92%, 93%, 94%, 95%, 96%, 97%, 98%, 99%, or greater. The range 90-99% includes all values between 90% and 99% including integer and non-integer values.

Immobilized amphipathic polycations described herein and soluble cationic antimicrobials likely share a similar mechanism of attacking bacteria. Polycations, such as polymyxin B and antimicrobial cationic peptides, displace the divalent cations that hold together the negatively charged surface of the lipopolysaccharide network, thereby disrupting the outer membrane of Gram-negative bacteria like *P. aeruginosa* and *E. coli*. This in itself might be sufficient for a lethal outcome. It is also possible that, having destroyed the outer membrane permeability barrier, the cationic groups of the tethered polymers further penetrate into the inner membrane, producing leakage. Such "self-promoted penetration" with the subsequent damage of the inner membrane has been described for polymyxin. The action of immobilized polycations against the Gram-positive bacteria *S. aureus* and *S. epidermidis* probably requires penetration of the cationic groups across the thick cell wall to reach the cytoplasmic membrane. Bactericidal action of amphipathic cationic antiseptics, such as benzalkonium chloride or biguanidine chlorhexidine, against Gram-positive bacteria is due primarily to the disruption of the cytoplasmic membrane. The cell wall of *S. aureus* is some 30 nm thick. Therefore, polymers having an average length of at least 10-20, preferably 15-20 nm should be able to penetrate the cell wall.

The antimicrobial activity of the claimed coatings is a consequence of their polymeric composition. Hydrophobic polycationic polymers possess a combination of charge and hydrophobicity that allows them to resist, by means of electrostatic repulsion, hydrophobic interchain aggregation, and yet able to penetrate bacterial cell membranes.

III. Methods of Making Coated Substrates

As discussed above, the polymer can be covalently or non-covalently associated with the surface. For those embodiments where the polymer is covalently associated with the surface, the polymer can be attached to the surface by functionalizing the surface with a reaction functional group, such as a nucleophilic group, and reacting the nucleophilic group with a reaction functional group on the polymer, such as an electrophilic group. Alternatively, the polymer can be functionalized with a nucleophilic group which is reacted with an electrophilic group on the substrate surface.

In particular embodiments, the polymer is non-covalently associated with the surface. The polymer can be applied to the surface by spraying, wetting, immersing, dipping, painting, bonding or adhering or otherwise providing a surface with a compound with the hydrophobic, polycationic polymer. In one embodiment, the polymer is applied by spraying, painting, or dipping or immersing. For example, an antimicrobial paint can be prepared by dissolving the polymer in a suitable solvent, and optionally sonicating the solution to ensure the polymer is completely dissolved. The device to be coated can be immersed in the polymer solution for a suitable period of time, e.g., 5 seconds, followed by drying, such as air drying. The procedure can be repeated as many times as necessary to achieve adequate coverage. The thickness of the coating is generally from about 1 inn to about 1 cm, preferably from about 10 nm to 1 mm, more preferably from about 100 nm to about 100 microns.

The coating can be applied at the time the implant is manufactured or can be applied subsequent to implant manufacture. In some embodiments, the coating is applied to the implant immediately prior to use of the implant. This is referred to an intraoperative coating. "Immediately prior", as used herein, mean within 1, 2, 5, 10, 15, 20, 30, 45, 60, 75, 90, 120, 150, 180 minutes or greater of implantation. In some embodiments, the implant is coated at the hospital, e.g., in the operating room, with 20, 15, 10, or 5 minutes of implantation. Implantation immediately prior to use may overcome limitations of implants coated at the time of manufacture, such as damage of the coating during storage and/or transportation of the device and/or decrease in the efficacy of the coating over time as the coating is exposed to environmental conditions, which may be harsh (e.g., high temps, humidity, exposure to UV light, etc.).

IV. Methods of Using Coated Implants

A variety of implants can be coated with one or more of the polymers described herein to prepare an antimicrobial surface. A schematic showing the research methodologies for evaluating the efficacy of the implants is shown in FIG. 1. The implants can be orthopedic or dental implants, cardiovascular implants, or ENT implants. The implants can be implanted into a mammal, such as a human, live stock, such as cows, sheep, or horses, or domesticated animals, such as dogs or cats. Veterinarian applications are particularly important since infection is often associated with injury, particularly to hard tissue such as bone.

A. Orthopedic Implants

The implants described herein can be used to replace bone or provide fixation to bone, replace articulating surfaces of a joint, provide abutment for a prosthetic, or combinations thereof or assist in replacing bone or providing fixation to bone, replacing articulating surfaces of a joint, providing abutment for a prosthetic, including dental applications, and combinations thereof.

As shown in the examples below, clinical observations, digital radiography, and a battery of well-accepted ex vivo analytical methods show that the presence of a hydrophobic polycationic polymer coating, such as N,N-dodecyl,methyl-PEI coating, on the surface of a metal implant was effective in eliminating the clinical signs of infection in vivo in a large animal infection model. Moreover, the coated plates supported bone healing, and in fact decreased healing times, even in the presence of significant bacterial contamination compared to a control.

For example, the antimicrobial efficacy of coated implants was evaluated in vitro by inoculating uncoated and coated plates with $S.$ $aureus$. The surface morphology of the plates was examined by scanning electron microscopy (SEM) for evidence of bacterial biofilm formation and correlated these findings with microbiological culture results and colony counts derived from the sonicates obtained during specimen production. All inoculation wells for the N,N-dodecyl,methyl-PEI-coated plate pieces were clear and the sonicates yielded very few colonies. The polycation coated metal surfaces were largely devoid of bacteria with only occasional evidence of a cluster of a few planktonic bacteria.

In contrast, inoculation wells for plain (uncoated) plate pieces were cloudy resulting in high colony counts from the sonicates. Cloudy wells and colony count data corroborated SEM observations where bacterial biofilm was covered with extracellular matrix that appears similar to the exopolysaccharide matrix described in other studies that assessed bacterial biofilms with SEM.

To verify these observations in vivo, a large animal (sheep) infection model for long-bone osteosynthesis in sheep using LCPs, a commonly used method of fixation of bones to stabilize major fractures during the healing process, was used. The effects of N,N-dodecyl,methyl-PEI-coated LCPs were compared with those of the uncoated LCPs on fracture healing (with no introduced bacteria) at the macroscopic (gross morphology) and microscopic (histological) levels for a period of three months postoperative. Comparative qualitative radiographic examination and histological analysis of fracture callus architecture revealed no appreciable difference between osteotomies treated with uncoated and coated LCPs. N,N-dodecyl,methyl-PEI coatings neither negatively impacted soft or calcified tissue physiology nor altered the healing response over at least a three-month period.

After four weeks of postoperative survival, the sheep were euthanized and operated tibiae were explanted for ex vivo analyses. No hardware failures were detected. Aseptic dissection and gross evaluation of the osteotomy region and associated soft tissues revealed stark differences between animals receiving N,N-dodecyl,methyl-PEI-coated and uncoated LCPs. Macroscopic assessment of the fracture site for the treatment cohort indicated healthy tissue recovery without evidence of infection and a uniformly bridging bony callus. In contrast, the control cohort exhibited a prevalence of infection in all animals, which is supported by positive bacterial cultures for $S.$ $aureus$ from the osteotomy sites. In addition, the osteotomy sites in control animals were mechanically unstable as evidenced by the persistence of the osteotomy compared to those in the treatment cohorts. Overall, the explant scores evaluating the gross appearance of the osteotomy sites, overlying fracture plates, and surrounding soft tissue envelopes were much lower for the treatment cohort than for the control group of sheep.

Histological scoring was performed by a blinded veterinary pathologist and showed a significantly lower histology score consistent with improved bone healing and absence of infection in treatment animals, as compared to those in the control group ($p=0.0002$). Some of the characteristic morphological findings in the treatment groups included various degrees of osteotomy bridging consisting of woven bone (85%), islands of hyaline cartilage (10%), and fibrovascular tissue (5%). In general, inflammation was very sparse and of no significance in the treatment group. The components of cells for the treatment groups consisted of predominantly lymphocytic, plasmacytic, with some eosinophils and rare neutrophils. The main features in the control group comprised of large inflammatory aggregates of necrotic neutrophils in the medullary space, and concentrated at the plated cortex extending through fibrous tissue in the osteotomy gap. There was no endosteal callus present; this was a hallmark difference between the treatment and control groups and also correlated with the presence of osteomyelitis. There was evidence of large clusters of bacteria seen within the canaliculi and Haversian' canals of dead bone that opened to the osteotomy site.

When comparing cohorts "treatment vs. control", the former scored significantly lower with overall less inflammation of the soft tissue envelope, more bridging callus formation, no macroscopic evidence of purulent debris, and a macroscopically more stable osteotomy at one month. Microbiological analyses from culture swabs obtained during the aseptic tissue harvest revealed *S. aureus* colonies where culture swabs were positive (all control animals). Tibiae from control animals showed overt signs of infection accompanied by frank pus, necrotic tissue, destruction of cortical bone, and an unstable osteotomy site resulting in increased score values.

SEM revealed several important observations regarding the coated implants: (1) the coated implants retained their antimicrobial activity upon re-exposure after explantation from the animals; (2) the bacterial cultures obtained at time of plate explantation were negative; and (3) the plate surfaces had only single planktonic bacteria when compared with biofilm laden control plates.

Clinically more important, for those animals treated with the coated implant, the bone ends were fused and well on their way to healing when compared to the control cohorts where bone ends were unstable. The coated implants resulted in uncomplicated fracture healing (e.g., fusion of two bone interfaces) in the presence of bacterial contamination and/or infection. The coated implants also decreased postoperative infection rates by protecting them from serving as a host environment for bacterial colonization. This is believed to be the first report demonstrating safety and efficacy of an antimicrobial surface modification methodology in a clinically relevant large animal model. Such an observation was unexpected in view of the fact that blood proteins are typically negatively charged and therefore are expected to adsorb onto the surface due to electrostatic interactions with the polycationic polymers. This protein absorption does not prevent the coated implants described herein to prevent infection and/or biofilm formation while decreasing healing times in the presence of such infections.

The implants described herein can be used to treat open fractures or wounds where infection is present or which are prone to infection, particular traumatic injuries, such as battlefield injuries or injuries that occur at a location which is removed from medical facilities. In such situations, treatment must be rendered immediately in order to stabilize the fracture. The conditions under which treatment is rendered are typically not sterile and so the potential for infection is high. Further, it may be some time before the patient reaches a medical facility where the wound can be closed. Therefore, the use of the implants descried herein can be used to effectively treat such injuries in the presence of infection.

Next, we investigated if the N,N-dodecyl,methyl-PEI surface derivatization of stainless steel orthopedic hardware remained stable when exposed to conventional methods of sterilization, e.g., steam and ethylene oxide (EO) following coating of plate chip samples. When bacterial cell counts were assessed to determine the effect of either sterilization methodology, all N,N-dodecyl,methyl-PEI were found to have significantly less bacterial colonization compared to the negative controls (p=0.001). The N,N-dodecyl,methyl-PEI-steam group was less likely to have bacterial growth when compared to the N,N-dodecyl,methyl-PEI-EO group or the N,N-dodecyl,methyl-PEI-positive control groups (p=0.027). There was no significant difference in bacterial cell counts between N,N-dodecyl,methyl-PEI-EO and N,N-dodecyl,methyl-PEI-positive control groups. SEM analysis of implant surfaces revealed abundant amounts of bacterial cocci and biofilm formation on negative controls.

SEM analysis of N,N-dodecyl,methyl-PEI inserted into equine cortical bone revealed the coating to be stripped from the cutting threads at the bone-screw interface. Bacterial colonization of N,N-dodecyl,methyl-PEI was limited to small single colony formation and the location of these cocci was restricted to the screw threads. Images of the negative controls had evidence of biofilm formation and bacterial overgrowth. These SEM findings were statistically supported by bacterial cell counts in the respective experimental groups (p=0.002).

B. ENT Implants

Ears, nose, and throat implants can also be coated with the polymers described herein. Tympanostomy tubes were coated with a linear N,N-dodecyl,methyl-polyethylenimine (DMPEI) to form an antimicrobial surface. Two types of commercially available tympanostomy tubes, Polyethylene POPE vent tube (PE) and Fluoroplastic Donaldson vent tube (FP) were coated with DMPEI and challenged with 104 CFU of *Haemophilus influenza, Moraxella catarrhalis*, and Methicillin-resistant *Staphylococcus aureus* (MRSA).

Both polyethylene and fluoroplastic tubes coated in DMPEI had significantly less biofilm formation compared to the controls that were challenged with MRSA, *H. influenza*, and *M. catarrhalis*, confirmed by bacterial count and SEM. For MRSA and *H. influenza*, bacterial count on PE and FP tubes were less than $3 \times 10^{13}$ for tubes coated with DMPEI vs. the controls having greater than $8 \times 10^{13}$, p<0.005. Similar results were obtained for PE and FP tubes challenged with *M. catarrhalis* with significantly less bacterial growth on tubes coated with DMPEI. Qualitative evaluation by SEM confirmed near absence of biofilm formation on the DMPEI coated tubes.

EXAMPLES

Materials and Methods

Polymer Synthesis and Coating

All chemicals used herein, unless otherwise noted, were from Sigma-Aldrich Chemical Co. and used without further purification.

Linear PEI was prepared by acid hydrolysis of poly(2-ethyl-2-oxazoline) as described in the literature. Subsequent N-alkylation of PEI with dodecyl and methyl moieties yielded the hydrophobic polycation N,N-dodecyl,methyl-PEI.

To prepare the microbicidal paint, 3.0 g of this polymer was dissolved in 60 mL of butanol with a 10-min sonication. Hardware (described below) was coated by immersion in the polymer solution for 5 sec, followed by air drying; this painting procedure was repeated three times.

Example 1

In Vitro Challenge Assay

Metallic Orthopedic Pins

To scale-up and validate the aforementioned coating procedure for orthopedic hardware, two different metals were used: (1) commercially pure Titanium (cpTi) and (2) stainless steel 316L. Bone plate chips measuring approximately 1 cm by 1 cm were cut transversely from orthopedic bone plates (Locking Compression Plates (LCP); Synthes, West Chester, Pa.) using a diamond saw (EXAKT System, Norderstedt, Germany). They were divided into two groups: control (no surface modification) and treatment (coated with N,N-dodecyl,methyl-PEI) groups, with all assays run in triplicate.

For the bacterial challenge assay, Staphylococcus aureus (ATCC 25923; this strain of S. aureus is susceptible to commonly used antimicrobials) was cultured in trypticase soy broth (TSB) with shaking at 37° C. for 16 h. A 1-mL aliquot of this culture was sub-cultured with 9 mL of fresh TSB for an additional 2 h prior to dilution to 0.5 McFarland Standard turbidity meter equivalent to $1 \times 10^8$ colony-forming units (CFU) and then serially diluted to $1 \times 10^4$ CFU/mL. The control and N,N-dodecyl,methyl-PEI-coated plate chips were incubated in 5 mL of $10^4$ CFU of S. aureus for 16 h at 37° C. The medium was then removed, and plate samples were washed with TSB three times to remove loose, non-adherent bacteria prior to re-incubation for 4 h to encourage adherent bacteria to proliferate. Sonicates were cultured for microbiological analysis and colony counts were established to correlate findings from the SEM examination. For SEM, samples were washed extensively with PBS to remove loose bacteria, placed in 4% paraformaldehyde for 2 h, and dehydrated in a series of ethanol solutions in water (10-100% (v/v)) before being placed in Freon 113 until dry. The samples were sputter-coated and evaluated under the SEM at 3,000- and 5,000-fold magnifications.

Tympanostomy Tubes

Two types of commercially available tympanostomy tubes, Polyethylene POPE vent tube (PE) and Fluoroplastic Donaldson vent tube (FP) were coated in vitro with DMPEI and challenged with $10^4$ CFU of Haemophilus influenza, Moraxella catarrhalis, and Methicillin-resistant Staphylococcus aureus (MRSA). Controls were the same two types of vent tubes without the DMPEI coating. Bacterial cell count and scanning electron microscopy (SEM) were performed on the controls and DMPEI coated tubes.

Both polyethylene and fluoroplastic tubes coated in DMPEI had significantly less biofilm formation compared to the controls that were challenged with MRSA, H. influenza, and M. catarrhalis, confirmed with bacterial count and SEM. For MRSA and H. influenza, bacterial count on PE and FP tubes were less than $3 \times 10^{13}$ for tubes coated with DMPEI vs. the controls having greater than $8 \times 10^{13}$, $p<0.005$. Similar results were obtained for PE and FP tubes challenged with M. catarrhalis with significantly less bacterial growth on tubes coated with DMPEI. Qualitative evaluation by SEM confirmed near absence of biofilm formation on the DMPEI coated tubes.

N,N-dodecyl,methyl-polyethylenimine coating on tympanostomy tubes inhibits bacterial colonization and confers protection to the tympanostomy tubes from biofilm formation. Prevention of biofilm formation may confer significant decrease in the rate of infection in a clinical setting.

In Vivo Assays

Figure 2:
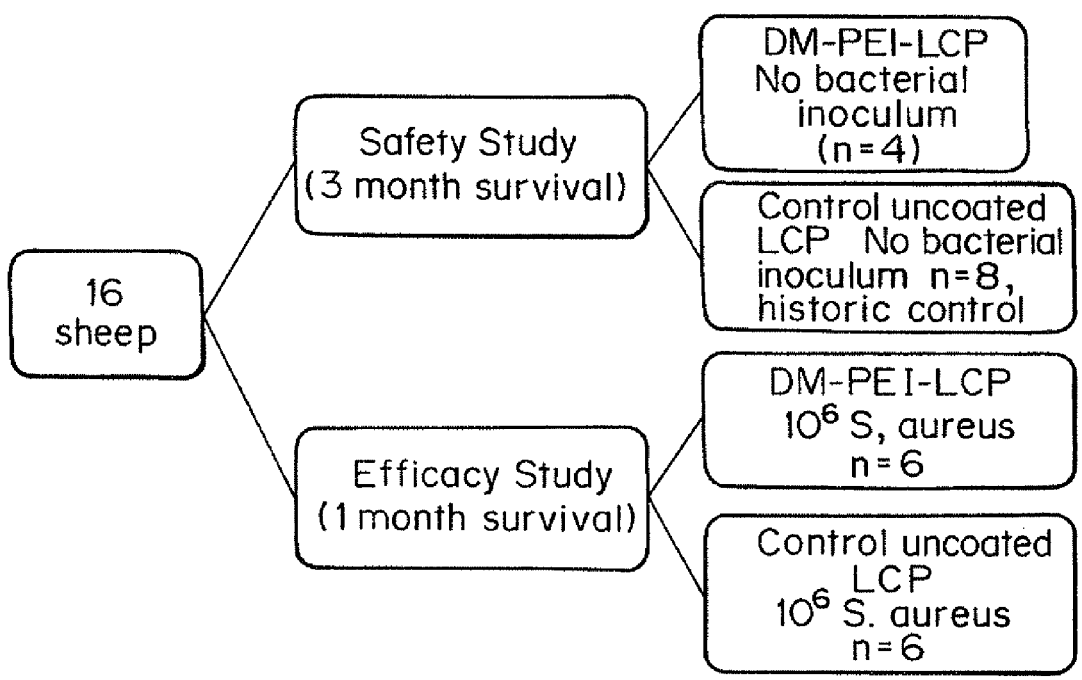
FIG. 2 is a schematic showing cohort breakdown of animals used in the study in Example 1.

For the in vivo study, a total of 16 locking compression plates were used. The 92 plate coating (n=10) was performed intraoperatively under aseptic conditions. Aliquots of 1-cm plate chips from locking compression plates (n=16) were run in parallel with each surface modification intraoperatively. Using these plate samples for in vitro verification of the N,N-dodecyl,methyl-PEI coatings allowed for quality control of the coated plates used in the animal studies. These plate aliquots were processed using the protocols described above for the in vitro assays (incubated with S. aureus for 16 h, washed to remove loose non-adherent bacteria, and reincubated for another 4 h to encourage adherent bacteria to proliferate) and for preparation for SEM analysis. The cohort breakdown of animals used in this study is illustrated in FIG. 2.

Animal Model

A sheep infection model for long bone plate osteosynthesis was previously developed and validated. The objective was to model and thus recapitulate the clinical signs of bone infection, such as pain, soft tissue swelling, fracture callus lysis, medullary canal resorption, and delayed bony union. Briefly, under general anesthesia, sheep underwent unilateral tibial middiaphyseal osteotomies using a medial approach. The osteotomy was repaired with an 8- or 9-hole LCP. After complete soft tissue closure, a temporary indwelling silastic catheter was inserted into the osteotomy site and inoculated with a 2.5-mL suspension of $10^6$, $10^8$, or $10^{10}$ colony-forming units (CFUs)/mL of S. aureus ATCC 25923. (The most commonly used staphylococcal strains in animal models of osteomyelitis include ATCC 29213, 25923, 6538P). Another objective was to develop and validate a long-bone infection model resulting in clinical-, radiographic-, gross-pathologic- and histologic signs consistent with septic osteomyelitis and thus exhibiting impaired fracture healing when compared to controls presented with radiographic-, gross-pathologic-, and histologic evidence of normal fracture healing with various degrees of bridging callus and a stable osteotomy.

Animal Surgeries

All animal procedures were reviewed and approved by the Institutional Animal Care and Use Committee of the University of Pennsylvania (Philadelphia, Pa.).

The experiments were broken down into two parts: (1) evaluating the impact of N,N-dodecyl,methyl-PEI-coated bone plates on fracture healing using four skeletally mature (2.5-3.5 years) Dorset-cross ewes in an unchallenged (no bacteria) tibial osteotomy model for three months postoperative (safety study). These data were compared to historic cohort data from tibial osteotomy bone healing studies in sheep (n=4) conducted previously and the impact of the coated bone plates with that of non-modified bone plates in a bacterial challenge (infected) tibial osteotomy model using 12 skeletally mature Dorset-cross ewes for one month postoperative (efficacy study).

Surgical Procedures

Perioperative analgesia in all sheep consisted of flunixin meglumine (1.1 mg/kg), buprenorphine hydrochloride (0.01 mg/kg) and transdermal fentanyl patches (2.5 µg/kg). All animals received one preoperative dose of antimicrobials consisting of intravenous ceftiofur (5.0 mg/kg) and intramuscular procaine penicillin (22,000/IU). The animals were placed under general anesthesia in left lateral recumbency. The left tibia was clipped and aseptically prepared for surgery. A medial approach was used to the tibia, and a short segment of the periosteum was circumferentially elevated at the mid-diaphysis of the tibia. A unilateral mid-diaphyseal transverse tibial osteotomy was performed using a 0.6-mm oscillating bone saw (Synthes, West Chester, Pa.). The osteotomy was reduced using a 4.5-mm eight or nine hole cpTi (safety study) or stainless steel (efficacy study) narrow locking compression plate (LCP) applied over the medial aspect of the tibia. The overlying fascia and soft tissue were closed using 2-0 polyglactin 910 (Johnson and Johnson), and a sialastic 16-g catheter was incorporated into the closure at the level of the osteotomy. Stainless steel staples and cyanoacrylate tissue adhesive were used to seal the skin. Sheep enrolled in the efficacy study received 2.5 mL of $10^6$ CFUs of S. aureus via a sialastic catheter directed onto the osteotomy site. The catheter was then removed, and a sterile dressing and bi-valve splint were placed for recovery. Immediately postoperatively all animals received fentanyl transdermal patches (2.5 µg/kg) on their left antebrachium that was secured with a single layer of elasticon. All sheep in the study were evaluated twice daily by a veterinarian for general health, comfort and appearance of the surgical site. Daily examinations of each animal by the surgical veterinary team consisted of general demeanor, appetite, physical exam, appearance of and response to palpation of the surgical site and degree of lameness in the operated leg were individually recorded.

The four sheep enrolled in the safety arm of the study were euthanized at three months postoperative, while the twelve sheep in the efficacy arm of the study were euthanized at one month postoperative. The left hind limb was harvested at the hip joint followed by an aseptical preparation for a sterile explant procedure of the implant and the bony callus. The gross anatomical appearance of the surgical site in general and the soft tissue envelope and bone around the osteotomy site in particular were evaluated using a semi-quantitative scoring system (Table 2).

TABLE 2

Scoring System used for in vivo experiments
Histologic Criteria

Callus Formation - Periosteal
    Woven Bone (0% = 3; 1-30% = 2; 31-60% = 1; 61-100% = 0)
    Cartilage (0%-3; 1-30% = 2; 31-60% = 1; 61-100%=)
    Fibrovascular tissue (0% = 0; 1-30% = 1; 31-60% = 2; 61-100% = 3)
Callus formation -Endosteal
    Woven Bone (0% = 3; 1-30% = 2; 31-60% = 1; 61-100% = 0)
    Cartilage (0%-3; 1-30% = 2; 31-60% = 1; 61-100% = 0)
    Fibrovascular tissue (0% = 0; 1-30% = 1; 31-60% = 2; 61-100% = 3)
Osteotomy
    Bridging tissue
        Neutrophil infiltrate (0/–40x hpf = 0, 1/40x hpf = 1;
        2/40x npf = 2; 3/40x hpf = 3; >3/40x hpf = 4)
        Necrotic (yes = 1, no = 0)
    Bone ends
        % absent lacunae (0% = 0; 1-30% = 1; 31-60% = 2; 61-100% = 3)
    Marrow Changes
        % Fatty tissue (0% = 3; 1-30% = 2; 31-60% = 1; 61-100% = 0)
        Fibrovascular tissue (0% = 0; 1-30% = 1; 31-60% = 2; 1-100% = 3)
        Neutrophilic inflammation (no = 0, yes = 1)
    Bone Lysis (at low magnification 2x)
    Periosteal (0% = 0; 1-30% = 1; 31-60% = 2; 61-100% = 3)
    Endosteal (0% = 0; 1-30% = 1; 31-60% = 2; 61-100% = 3)
    Osteotomy (0% = 0; 1-30% = 1; 31-60% = 2; 61-100% = 3)

Explant Criteria (Gross-pathologic grading of osteotomy region)

| 1. Soft tissue envelope | 2. Plate in situ | 3. Osteotomy after plate removed |
|---|---|---|
| 0 = healed | 0 = no abscess | 0 = bridging callus & stable |
| 1 = inflammation | 1 = micro-abscesses in plate holes | 1 = bridging callus & unstable |
| 2 = mild necrotizing inflammation | 2 = abscess covering <50% plate | 2 = non-bridging callus & unstable |
| 3 = severely necrotic debris/devascularized | 3 = abscess covering >50% plate | 3 = no callus & unstable |

Digital Radiographic Criteria

| Variable | Definition | Score |
|---|---|---|
| Periosteal reaction/lifting | +/present | 1 |
| | –/absent | 0 |
| Osteolysis | +/present | 1 |
| | –/absent | 0 |
| Sequestrum formation | +/present | 1 |
| | –/absent | 0 |
| Implant loosening | +/present | 1 |
| | –/absent | 0 |
| Soft tissue swelling | +/present | 1 |
| | –/absent | 0 |
| Callus | | |
| None | | 3 |
| Early callus (non-bridging) | | 2 |
| Bridging callus | <50% | 1 |
| | >50% | 0 |

A sterile culture was taken from sheep which received a bacterial inoculum at the level of the osteotomy before implant removal. Then implants were removed aseptically, sectioned into 15-mm pieces using a diamond saw (EXAKT System), and samples were prepared for bacterial colony counts and SEM visualization as described in the in vitro section above. The bony callus was harvested, placed in 10% neutral buffered formalin, and fixed for calcified tissue histology.

Hematology and Serum Chemistry

A venous blood sample was collected for routine preoperative hematology, fibrinogen, and serum chemistry. Fibrinogen levels were analyzed using a HEMOSIL® PT1 Fibrinogen Kit (Beckman Coulter, Brea, Calif.) at weekly intervals until sacrifice of the animals.

Imaging

In Vivo Digital Radiography:

Standard caudocranial and lateral radiographs (Sound-Eklin Digital X Ray, Carlsbad, Calif.) of the left tibia in the standing animal were obtained immediately postoperative and at one month intervals until sacrifice. Radiographic assessment was carried out by three blinded observers who graded the studies according to a semi-quantitative scoring system for radiographic signs of infection and evaluation of fracture healing (Table 3).

TABLE 3

Semi-quantitative radiographic and histological scores

| Stastistical Analysis | Mean Score Coated | Mean Score Control | p-value |
|---|---|---|---|
| Radiographic Scores | 0.5 | 0 | 0.187 |
| Histologic Scores | 1.25 | 0 | 0.079605 |

| N1 | N2 | u | P(two-tail) | P(one-tail) |
|---|---|---|---|---|
| 4 | 4 | 14 | 0.342858 | 0.171429 |
| Normal approx. z = 1.1547 | | | 0.248214 | 0.124107 |

Ex Vivo Micro-Computed Tomography:

The tibias from control and treatment sheep were blocked to contain the mid-diaphyseal osteotomy site as region of interest and scanned using a Scanco80 scanner (µCT-80; Scanco Medical, Bassersdorf, Switzerland) with a voxel isotropic resolution of 50 µm, X-ray energy of 55 kVp, and current of 145 µA at medium resolution. Scan 179 time ranged from approximately 3.0 to 3.9 h per sample and accounted for 1024 projections/180 degrees and 2048 charge coupled device detector array. A calibration phantom of hydroxyapatite was used to detect variances in density and volume of the X-ray source over time. Segmented images were obtained using a Gaussian filter with a sigma=1.0, support=0.8, and threshold=300. Reconstructed 3-D images were compiled to display differences in morphology of the osteotomy site with respect to the treatment (coated hardware) and control (non-coated hardware) cohorts.

Histology

The tibial osteotomy region from all animals was processed for non-decalcified histology and embedded in poly(methyl methacrylate) resin. Plastic blocks were cut on a rotary microtome (Leica Microsystems, Nussloch, Germany) in the sagital plane at 5 to 8 µm, mounted, and stained. All samples were stained with hematoxylin and eosin to assess tissue morphology of the soft tissue envelope and within the osteotomy region. Toluidine blue was used to evaluate the degree of bony healing at the level of the osteotomy. Brown and Brenn stains were used to determine whether bacteria were present within the bone. Histological evaluation was performed by a blinded histopathologist analyzing callus architecture, cellular infiltration, and tissue remodeling response at three months postoperative for the safety and at one month postoperative for the efficacy studies, respectively. The degree of fracture healing was evaluated in each group using a point scale (Table 4).

TABLE 4

Mean radiographic-, explant-, microbiology-, and histopathology scores

| Statisical Analysis | Mean Score Treatment | Mean Score Control | p-value | Standard Error Treatment | Standard Error Control |
|---|---|---|---|---|---|
| Radiographic Scores | 1.77 | 3.44 | P = 0.0006 | 0.25 | 0.11 |
| Explant Scores | 0.67 | 5.67 | P = 0.0005 | 0.42 | 0.76 |
| Microbiology Scores | 1 | 3 | P = 0.025 | 0.63 | 0 |
| Histopathology Scores | 0.67 | 5 | P = 0.0007 | 0.33 | 0.51 |

Statistics

The safety data were derived from two groups of 4 animals each to compare the impact of N,N-dodecyl,methyl-PEI coating on fracture healing. Using an unpaired t-test, this sample size has an 80% power to detect a difference between means (coated vs. non-coated) using the semi-quantitative radiographic- and histologic scoring systems. The efficacy study data were derived from two groups of 6 animals each. Using an unpaired t-test, this sample size has a 90% power to detect a difference between the means (coated vs. uncoated) using the point scale grading systems shown in Table 2. Statistical comparisons were made where applicable with a Student's t-test with a level of significance set at p<0.05. The raw scores from subjective and objective measurements obtained by blinded observers for gross-pathology, radiography, and histology were converted to a point scale, where the lowest sum of points equaled the best possible result. Inter-observer agreement was determined, and statistical analysis was done after data conversion. A Mann-Whitney test for non-parametric data was performed where applicable.

Results and Discussion

In Vitro Studies

Figure 3:
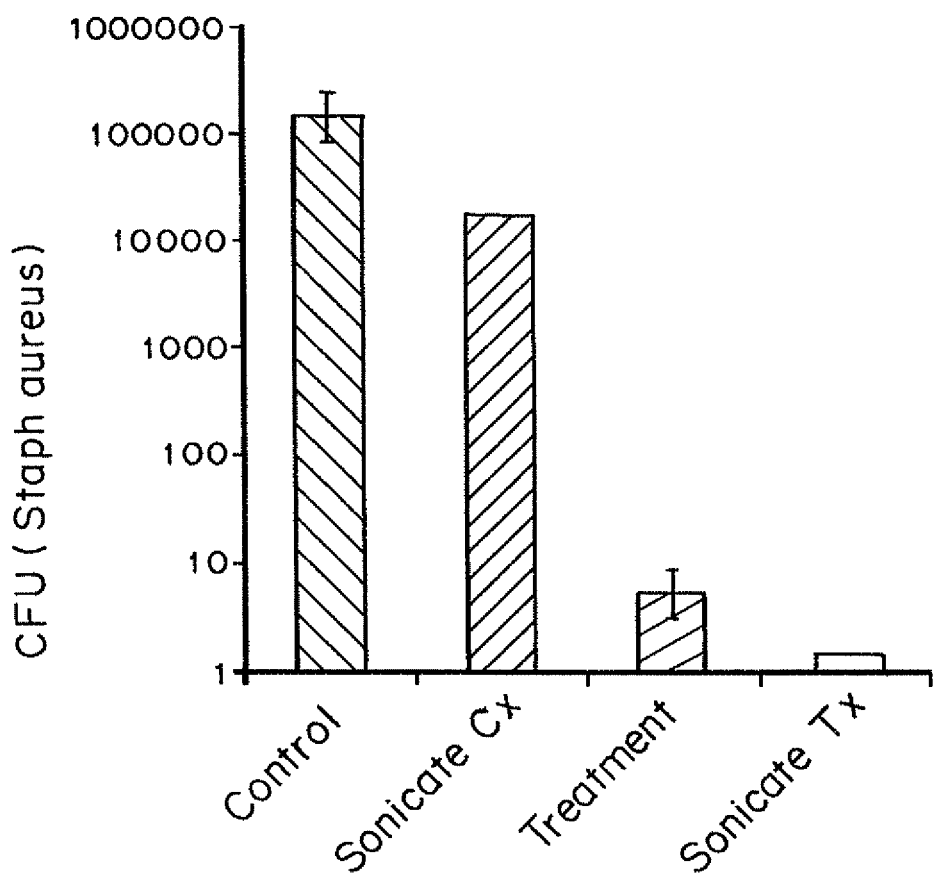
FIG. 3 is a graph showing colony counts from coated (treatment) and uncoated (control) LCP chips challenged with S. aureus in vitro. To examine and compare the activity of the N,N-dodecyl,methyl-PEI-coated and uncoated LCP chips against adherent organisms samples were incubated in 5 mL of 104 11 CFU of S. aureus for 16 h at 37ÿC. The medium was then removed, and plate samples were washed to remove loose, non-adherent bacteria prior to re-incubation for 4 h to encourage adherent bacteria to proliferate. Sonicates were cultured for microbiological analysis, serial diluted and spiral plated for cfu enumeration. Mean viable cfu (+SEM) recovered from inoculum of LCP chip cultures are shown for growth control (grey bars) with sonicates of uncoated and coated LCP chips respectively (black bars).

Scaling up from the in vitro testing modality to a biologically-meaningful anatomical scale model is a pivotal step in the translation of a new orthopedic technology. Thus prior to in vivo experiments, metal chips cut from either stainless steel or titanium locking compression plates (LCPs) were used to validate the antibacterial efficacy of N,N-dodecyl,methyl-PEI coatings in vitro. Plain and polycation-coated plate pieces were inoculated with S. aureus and the antibacterial efficacy of the pieces was evaluated. Specifically, the surface morphology of the plate pieces was evaluated by SEM for evidence of bacterial biofilm and the findings were correlated with microbiological culture results and colony counts derived from the sonicates obtained during specimen preparation (FIG. 3).

All inoculation wells for the N,N-dodecyl,methyl-PEI-coated plate pieces were clear, and the sonicates yielded very few colonies. Polycation-coated metal surfaces were largely devoid of bacteria with only occasional evidence of a cluster of a few planktonic bacteria. In contrast, inoculation wells for plain plate pieces were cloudy resulting in high colony counts from the sonicates. Cloudy wells and colony count data corroborated the SEM observations where bacterial biofilm was covered with extracellular matrix that appears similar to the exopolysaccharide matrix described in other studies that assessed bacterial biofilms with SEM. The quality control criteria for successfully derivatized hardware surface were met by observing bactericidal properties and lack of biofilm formation upon bacterial challenge of the coated samples. In contrast, uncoated samples were colonized by adhering bacteria, followed by biofilm formation.

In Vivo Studies

To verify the in vitro observations in vivo, an infection model for long-bone osteosynthesis in sheep using LCPs, a commonly used method of fixation of bones to stabilize major fractures during the healing process, was used. While no ideal model for osteomyelitis does exists, for translational purposes the animal needs to be large enough to withstand use of human orthopedic implants. It also should recapitulate a putative clinical setting, such as perioperative bacterial contamination of the surgical sites, implant colonization with biofilm and infection of surrounding tissues exhibiting an impaired fracture healing response.

Sheep have been used as models of orthopedic infection as well as models of chronic osteomyelitis. Orthopedic models utilizing sheep and goats are well accepted because their larger bone and intra-medullary canal size allow for evaluation of fixation devices that otherwise would need to be modified for use in such smaller animals as rabbits or rats (e.g., external fixators and intramedullary nails). While there are various infection models for intramedullary nailing and external fixators, there is little information for infected internal plate fixation available. Some of the clinical signs of bone infection included: (i) radiographic signs consistent with septic osteomyelitis, (ii) local soft and hard tissue destruction and abscess formation, (iii) implant colonization and biofilm formation, and (iv) an impaired fracture healing response resulting in a delayed or non-union of the osteotomized bones.

A refined and validated mid-diaphyseal osteotomy infection model for plate osteosynthesis in sheep was used to study the effects of coated implants in combination with existing trauma hardware. With this model, infection was consistently achieved and a resulting non-union of the osteotomized tibia in 100% of the control animals was observed.

In the in vivo study, the practicality of the hydrophobic polycationic coating (e.g. N,N-dodecyl,methyl-PEI) for conventional trauma hardware, with particular attention to any putative detrimental effects of the coated LCPs on fracture healing with and without bacterial infection, was evaluated. A well-accepted mid-diaphyseal tibial osteotomy model in skeletally mature sheep was used. The mid-diaphyseal transverse cut across one tibia simulated long bone trauma, which was repaired with LCPs that were either uncoated or coated by immersion in a solution of the hydrophobic polycation in butanol, followed by brief drying.

The effects of N,N-dodecyl,methyl-PEI-coated LCPs were compared with those of the uncoated ones on fracture healing (with no introduced bacteria) at the macroscopic (gross morphology) and microscopic (histological) levels for a period of three months postoperative. Converting the radiographic grading and histological analysis of fracture healing to a point scale revealed no difference between osteotomies treated with uncoated and coated LCPs (Table 3). Osteotomy repaired with a plain plate and a coated plate were compared by observing two representative sagital sections of the respective osteotomy sites at three months postoperative at a 2.5× magnification. The von Kossa staining mineralized tissue black, also emphasizes the still irregular "lacy" architecture of the newly formed woven bone in the modelling osteotomy sites. Microscopically, the gap between the osteotomized cortices was filled with newly formed bone, cartilage, and connective tissue. The arrows delineate the interface between the osteotomized cortical bone and the osteotomy gap filled with newly formed bone. Along the osteotomy margins both resorption and new bone formation could be observed, and intense modeling was seen in the adjoining cortical bone. The relative amounts of newly formed bone, cartilage, and connective tissue in the different locations varied among the animals. However, there was no difference in the spatial and temporal patterns of new bone formation between the groups (Table 3). Therefore, the N,N-dodecyl,methyl-PEI coating neither negatively impacted soft or calcified tissue physiology nor altered the healing response over at least a three-month period.

Having established that the implanted coated LCPs have no adverse effect on fracture healing, the antimicrobial potency of the coated implants was evaluated in vivo. Coated and uncoated LCPs were applied intraoperatively under aseptic conditions in a sheep long-bone infection model. The bacterial inoculum of $S.$ $aureus$, in a much greater quantity ($2.5\times 10^6$ CFU) than would be encountered in a clinical setting, was introduced into the mid-diaphyseal tibial osteotomy site at the end of the surgical procedure. It should be noted that all surgical procedures performed were uncomplicated, and the animals recovered uneventfully from surgery and general anesthesia. Their postoperative recovery was uneventful, and all surgical sites healed without complications. The decision to administer one systemic dose of perioperative antimicrobials (ceftiofur sodium, a third generation cephalosporin) via indwelling intravenous catheter is supported by previous animal model development studies. It was observed that a single, perioperative dose of antimicrobial attenuated the clinical side-effects (high fever and lethargy) caused by the bacterial inoculum administered during surgery. However, it would not impact the infection rate at the surgical site. Animals with uncoated LCP in general exhibited more pain on palpation of their surgical sited when compared to animals treated with a coated LCP.

Figure 4:
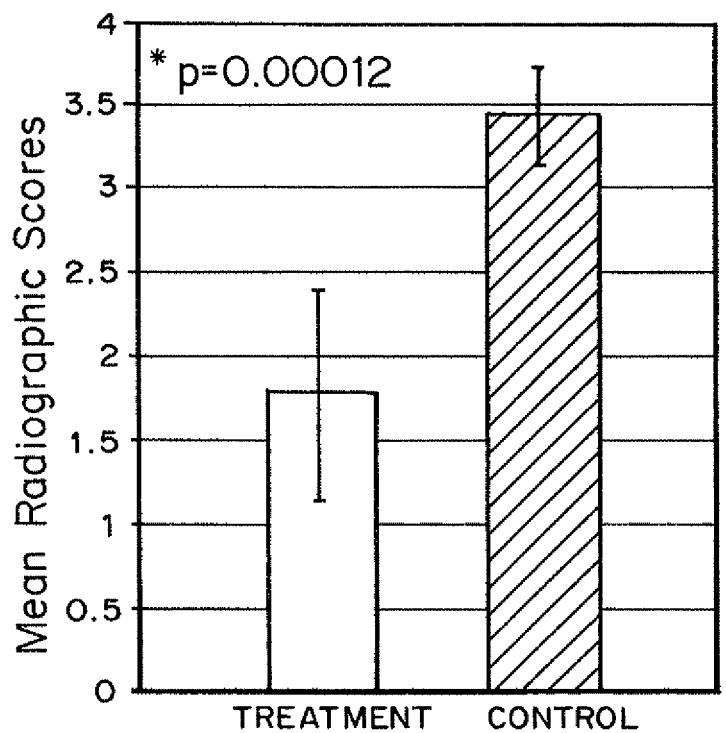
FIG. 4 is a graph showing the mean radiographic scores for all sheep by three independent reviewers. Resultant scores for the control group were significantly higher when compared to scores obtained from animals treated with N,N-dodecyl,methyl-PEI-coated LCPs ($p < 0.00012$). Treatment group animals overall showed signs of normal bone healing while control animals exhibited radiographic signs consistent with septic osteomyelitis.

Digital radiographs were obtained pre- and postoperative, as well as at time of sacrifice. Preoperative radiographs revealed no radiographic abnormalities in any of the animals, and immediate postoperative radiographs of the operated legs showed hardware to be in good order. Postoperative observations of the animals with uncoated LCPs revealed a clear trend of increased lameness on their operated leg compared to non-operated ones, supporting the clinical scenario of acute postoperative infection with its hallmark signs of soft tissue swelling, heat, and pain. Although these findings corroborate the radiographic-, gross- and histologic data, they were subjective clinical scores obtained during daily physical exams. Radiographic examinations before sacrifice at 30 days postoperative in this control group showed progressive signs of cortical thinning and disruption, periosteal reaction, and osteolysis consistent with septic osteomyelitis. By scoring these radiographic exams to standard predefined guidelines as discussed above, the results shown in FIG. 4 indicate that the animals receiving uncoated LCPs suffered debilitating adverse effects in their recovery, while those receiving the N,N-dodecyl,methyl-PEI-coated hardware exhibited significantly improved bone healing (p=0.0006). The radiographic scores consistent with septic osteomyelitis strongly support the clinical findings of lameness due to pain in the operated leg; they are also well aligned with the ex vivo findings discussed below.

After four weeks of postoperative survival, the sheep were euthanized and operated tibiae were explanted for ex vivo analyses. No hardware failures were detected. Aseptic dissection and gross evaluation of the osteotomy region and associated soft tissues revealed stark differences between animals receiving N,N-dodecyl,methyl-PEI-coated and uncoated LCPs. Macroscopic assessment of the fracture sites for the treatment cohort indicated healthy tissue recovery without evidence of infection and a uniformly bridging bony callus. In contrast, the control cohort exhibited a prevalence of infection in all animals, which is supported by positive bacterial cultures for *S. aureus* from the osteotomy sites. In addition, the osteotomy sites in control animals were mechanically unstable as evidenced by the persistence of the osteotomy compared to those in the treatment cohorts, which had a bridging callus and were grossly stable. At the time of the explant, the infected tibiae of the control cohort were all presented with a lytic and disorganized callus architecture that was grossly unstable, requiring care as to not disrupt the region of interest during specimen processing. Overall, the explant scores evaluating the gross appearance of the osteotomy sites, overlying fracture plates, and surrounding soft tissue envelopes were much lower for the treatment cohort than for the control group of sheep.

When comparing cohorts "treatment vs. control", the former scored significantly lower with overall less inflammation of the soft tissue envelope, more bridging callus formation, no macroscopic evidence of purulent debris, and a macroscopically more stable osteotomy at one month postoperative (Table 4, p=0.0005). Microbiological analyses from culture swabs obtained during the aseptic tissue harvest revealed *S. aureus* colonies where culture swabs were positive (all control animals). Tibiae from control animals showed overt signs of infection accompanied by frank pus, necrotic tissue, destruction of cortical bone, and an unstable osteotomy site resulting in increased score values.

3-D reconstructed Micro-CT views of tibiae from sheep with coated LCPs further support the inhibition of infection on the treatment side. Cortical midshaft sections containing the osteotomy from the treatment cohort were compared to those from control animals where severe changes in the local tissue architecture were observed. As seen in the former case, there was evidence of bridging callus with early mineralization, recapitulating the processes of endochondral ossification and remodeling. Images of bone stabilized by uncoated LCPs reveal a poorly organized, lytic callus with a markedly enlarged medullary canal and cortical thinning. These findings are consistent with a septic fracture site and well aligned with our observations obtained under light microscopy evaluating callus morphology of both cohorts.

Figure 5:
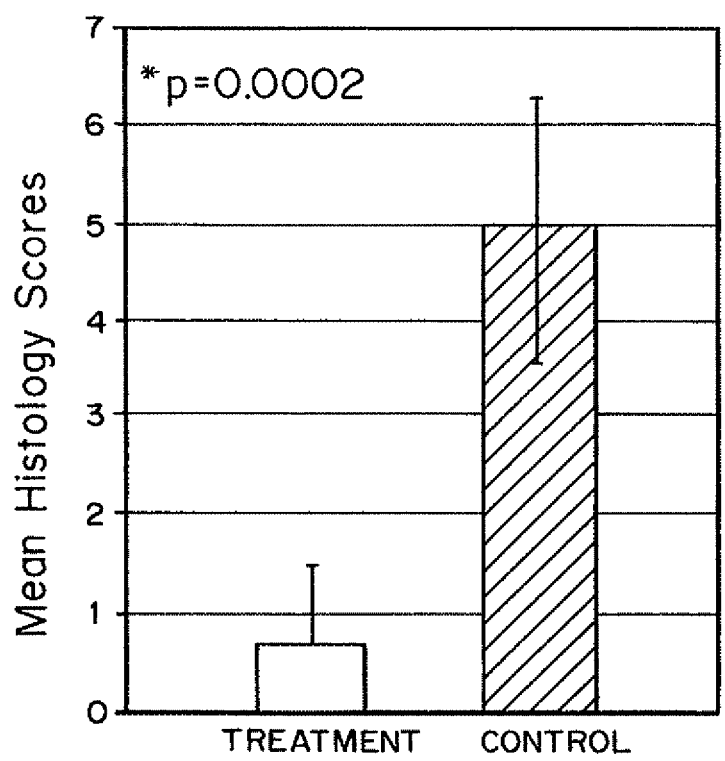
FIG. 5 is a graph showing mean histology scores for the treatment and control groups.

The histological scoring performed by a blinded veterinary pathologist shows a significantly lower histology score consistent with improved bone healing and absence of infection in treatment animals, as compared to those in the control group (FIG. 5, p=0.0002). Some of the characteristic morphological findings in the treatment groups included various degrees of osteotomy bridging consisting of woven bone (85%), islands of hyaline cartilage (10%), and fibrovascular tissue (5%). In general, inflammation was very sparse and of no significance. The components of cells for the treatment groups consisted of predominantly lymphocytic, plasmacytic, with some eosinophils and rare neutrophils. The main features in the control group comprised of large inflammatory aggregates of necrotic neutrophils in the medullary space, and concentrated at the plated cortex extending through fibrous tissue in the osteotomy gap. There was no endosteal callus present; this was a hallmark difference between the treatment and control groups and also correlated with the presence of osteomyelitis. There was evidence of large clusters of bacteria seen within the canaliculi and Haversian' canals of dead bone that opened to the osteotomy site.

The morphological changes are equally compelling when examined at the microstructural level. Sections from both cohorts comprised of diaphyseal bi-cortical bone associated with peri- and endosteal surfaces including the medullary canal were compared after staining with toluidine blue dye. The characteristic morphological observations in the treatment group, such as osteotomy bridging, formation of hyaline cartilage islands, and fibrovascular tissue (arrow), further support our findings at the macrostructural level. This demonstrates considerable improvement over the same region from sheep receiving an uncoated LCP where evidence is seen of severe cortical lysis with pockets containing debris accompanied by suppurative inflammation and a persisting osteotomy.

Because of the difficulty in assessing bacterial progression at the implant site during the postoperative period, the in vitro bactericidal efficacy of polycation coated stainless steel LCPs cut to a 1 cm length was validated qualitatively. Growth media incubated with uncoated LCP chips exhibited significant turbidity (indicative of bacterial growth), whereas media incubated with polycation-coated LCPs remained clear. Using these LCP chips in parallel with the LCPs applied in vivo to the tibiae during surgery, the efficacy of the coating was independently verified using SEM analysis of the plate samples for adherent bacteria and biofilm as described above. In addition, these results indicate that the in vivo observations of significantly improved healing in sheep receiving N,N-dodecyl,methyl-PEI coated LCPs are likely the result in eradication of infection at the site of implantation.

Finally, explanted LCPs were visualized using SEM. These recovered plates were placed into sterile saline at time of necropsy until further analyses. Uncoated plates (control cohort) displayed thick carpets of sessile bacteria covered by extracellular matrix that appears similar to the exopolysaccharide matrix described in the literature. This biofilm consistently covered >95% of the plate surface in control plates. In contrast, SEM analysis of the bone plates coated with N,N-dodecyl,methyl-PEI from the treatment cohort revealed no bacterial clusters. Once the LCPs from the in vivo study were sonicated to remove the cellular debris associated with the surrounding host tissues, the painted plates exhibited a smooth machined surface with occasional rare cocci and some residual cellular debris.

The totality of the diverse experimental evidence presented herein supports the view that painting with N,N-dodecyl, methyl-PEI protects implant surfaces from biofilm formation not only in vitro but also in vivo. It is noteworthy that the in vivo biofilm prevention occurs despite the abundance of blood proteins that can potentially block the bactericidal action of the N,N-dodecyl,methyl-PEI coating. We propose that, as in vitro, when pathogenic bacteria attempt to colonize the surface of an implanted coated bone plate, their adherence to the immobilized hydrophobic polycationic chains results in disruption of the outer cell wall and/or membrane leading to lethal structural changes and demise of the bacteria. The ensuing bacterial debris is then available to the host's immune surveillance, while the bone plate remains protected from assailing bacteria attempting to establish a recalcitrant biofilm.

Clinical observations, digital radiography, and a battery of well-accepted ex vivo analytical methods proved that the presence of a N,N-dodecyl,methyl-PEI coating on the surface of a metal implant was effective in eliminating the clinical signs of infection in vivo in a large animal infection model. Moreover, the coated plates supported bone healing even in the presence of significant bacterial contamination and completely prevented biofilm formation. Since the experimental strategy validated herein does not lead to emergence of resistant mutants at least in vitro, it may mitigate concerns about multi-drug resistant super-bugs commonly seen in conjunction with technologies based on conventional antimicrobials.

If device-associated infections covered by biofilm are the source of recalcitrant infections, then protecting hardware with a permanent coating could at least mitigate that risk. Conferring protection from pathogenic bacteria to an orthopedic implant of industrial size and geometry in vivo is promising for reducing implant-associated infections in the orthopedic patient.

We claim:

1. An implant comprising a polymeric coating on an outer surface of the implant, wherein the implant is selected from the group consisting of prosthetic implants, orthopedic implants, ear, nose, and throat implants, and cardiovascular implants, wherein the polymer forming the coating is an antimicrobial hydrophobic polycationic polymer selected from the group consisting of poly(4-vinyl-N-alkylpyridine), N,N-dialkylated branched polyethylene iminie, and N,N-dialkylated linear polyethylene imine polymers.

2. The implant of claim 1, wherein the implant comprises metallic material, metal oxides, synthetic or natural, cross-linked or non-crosslinked, polymeric materials, ceramics, porcelain, allogenic or xenogenic bone or bone matrix; genetically engineered bone; and combinations thereof.

3. The implant of claim 2, wherein the metallic material is selected from the group consisting of NiTi alloys, stainless steel, titanium or alloys thereof.

4. The implant of claim 2, wherein the implant comprises a non-degradable polymeric material.

5. The implant of claim 4, wherein the implant comprises a polymeric material selected from the group consisting of polypropylene (PP), polyethylene (PE), polyacetylene, cross-linked or non-crosslinked polystyrene, styrene-butadiene rubber, polytetrafluoroethylene, poly(vinyl chloride) (PVC), polyolefin copolymers, poly(methyl methacrylate), polyphenylene, polyacrylonitrile, carbon fiber, and blends or copolymers thereof.

6. The implant of claim 2, wherein the implant comprises a biodegradable polymeric material.

7. The implant of claim 6, wherein the implant comprises a polymeric material selected from the group consisting of collagen, cellulosic polymers, polysaccharides, poly(glycolic acid), poly(L-lactic acid) (PLLA), poly(lactide-co-glycolide) (PLGA), a polydioxanone (PDA), or racemic poly(lactic acid), polyurethane (PU), polycarbonates, polyetherketone (PEEK), polyesters, and polyamides (nylon).

8. The implant of claim 1 wherein the orthopedic implant is selected from the group consisting of Kirschner wire, bone plates, screws, pins, tacs, rods, nails, nuts, bolts, washers, spikes, buttons, wires, fracture plates, endo- and exoprostheses, intraosseous transcutaneous prostheses, spacers, mesh, implant abutments, anchors, barbs, clamps, suture, tubes of any geometry, and combinations thereof.

9. The implant of claim 1, wherein the ear, nose, or throat implant is selected from the group consisting of ear tubes, endrotracheal tubes, ventilation tubes, cochlear implants and bone anchored hearing devices.

10. The implant of claim 1, wherein the cardiovascular implant is selected from the group consisting of cardiac valves, alloplastic vessel wall supports, and total artificial heart implants.

11. The implant of claim 1 wherein the N,N-dialkylated branched polyethylene imine or N,N-dialkylated linear polyethylene imine is N,N-dodecyl,methyl-PEI or N,N-hexyl,methyl-PEI.

12. The implant of claim 1, wherein the weight average molecular weight of the N,N-dialkylated branched polyethylene imine or N,N-dialkylated linear polyethylene imine polymer is at least 20,000 g/mol.

13. The implant of claim 1, wherein the thickness of the polymer coating is between about 1 nm and about 1 cm.

14. The implant of claim 1, wherein the polymer coating is non-covalently associated with one or more outer surfaces of the implant.

15. The implant of claim 1, wherein the polymer coating is covalently associated with one or more outer surfaces of the implant.

16. A method of preventing infection while treating hard or soft tissue, the method comprising implanting the implant of claim 1.

17. The method of claim 16, wherein the coating is applied to the implant immediately prior to implantation.

18. A method of treating hard or soft tissue in the presence of an infection, the method comprising implanting the implant of claim 1.

19. The method of claim 18, wherein the coating is applied to the implant immediately prior to implantation.

20. The implant of claim 1 wherein the poly(4-vinyl-N-alkylpyridine) has the formula:

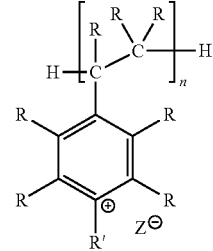

wherein, R for each occurrence is independently selected from the group consisting of hydrogen, alkyl, alkenyl, alkenyl, acyl, aryl, carboxylate, alkoxycarbonyl, aryloxycarbonyl, carboxamido, alkylamino, acylamino, alkoxyl, acyloxy, hydroxyalkyl, alkoxyalkyl, aminoalkyl, (alkylamino)alkyl, thio, alkylthio, thioalkyl, (alkylthio)alkyl, carbamoyl, urea, thiourea, sulfonyl, sulfonate, sulfonamido, sulfonylamino, and sulfonyloxy;

R' is selected from the group consisting of an alkyl, an alkylidene tethered to the surface, and an acyl tethered to the surface;

Z⁻ is independently selected from the group consisting of Cl, Br, or I; and n is an integer less than or equal to about 1500.

21. The implant of claim 20, wherein R' is selected from the group consisting of a $C_4$-$C_{12}$ alkyl, $C_6$-$C_{12}$ alkyl, and $C_6$-$C_{10}$ alkyl.

22. The implant of claim 1, wherein the weight average molecular weight of the poly(4-vinyl-N-alkylpyridine) polymer is at least 50,000 g/mol.

* * * * *

UNITED STATES PATENT AND TRADEMARK OFFICE
CERTIFICATE OF CORRECTION

| | |
|---|---|
| PATENT NO. | : 9,089,407 B2 |
| APPLICATION NO. | : 13/647107 |
| DATED | : July 28, 2015 |
| INVENTOR(S) | : Thomas P. Schaer, Suzanne Stewart and Alexander M. Klibanov |

Page 1 of 1

It is certified that error appears in the above-identified patent and that said Letters Patent is hereby corrected as shown below:

In the Claims:

Column 33, claim 1, line 18, replace "iminie" with --imine--.
Column 34, claim 20, line 43, replace "alkenyl, acyl" with --alkynyl, acyl--.

Signed and Sealed this
Twenty-first Day of June, 2016

Michelle K. Lee
*Director of the United States Patent and Trademark Office*